United States Patent
Schweinfest et al.

(12)

(10) Patent No.: US 6,720,413 B1
(45) Date of Patent: Apr. 13, 2004

(54) METHODS AND COMPOSITIONS FOR DIAGNOSIS AND TREATMENT OF CANCER

(75) Inventors: Clifford W. Schweinfest, Mount Pleasant, SC (US); Takis S. Papas, Charleston, SC (US); Paul L. Baron, Charleston, SC (US); Dennis K. Watson, Mount Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 09/034,418

(22) Filed: Mar. 4, 1998

Related U.S. Application Data
(60) Provisional application No. 60/039,980, filed on Mar. 4, 1997.

(51) Int. Cl.[7] ............................ C12N 15/12; C12N 1/00; C12N 5/10; C12N 15/63
(52) U.S. Cl. ................. 536/23.5; 435/320.1; 435/325; 435/252.3; 435/252.33; 435/69.1
(58) Field of Search ....................... 536/23.5; 435/320.1, 435/252.33, 252.3, 325, 69.1, 410

(56) References Cited

PUBLICATIONS

Schweinfest et al. Genbank Accession #AF000177. Bethesda, MD: National Library of Medicine. Jul. 1997.*
Callard et al. The Cytokine FactsBook. New York: Academic Press. p. 31, 1994.*
Almoguera et al., 1988, "Most Human Carcinomas of the Exocrine Pancrease Contain Mutant c–K–ras Genes", Cell 53:549–554.
Bansal and Sonnenberg, 1995, "Pancreatitis is a Risk Factor for Pancreatic Cancer", Gastroenterol. 109:247–251.
Baron et al., 1995, "Isolation and Characterization of Novel Genes with Elevated Expression in Pancreatic Cancer", Surgical Forum 46:485–488.
Berthélemy et al., 1995, "Identification of K–ras Mutations in Pancreatic Juice in the Early Diagnosis of Pancreatic Cancer", Ann. Int. Med. 123:188–191.
Boeck et al.,1996, "The Yeast Pan2 Protein is Required for Poly(A)–Binding Protein–Stimulated Poly(A)–Nuclease Activity", J. Biol. Chem. 271:432–438.
Caldas et al.,1994, "Frequent Somatic Mutations and Homozygous Deletions of the p16 (MTS1) Gene in Pancreatic Adenocarcinoma", Nature Genetics 8:27–32.
Cheng et al., 1996, "Amplification of AKT2 in Human Pancreatic Cancer Cells and Inhibition of AKT2 Expression and Tumorigenicity by Antisense RNA", Proc. Natl. Acad. Sci. USA 93:3636–3641.
Hahn et al., 1996, "DPC4, a Candidate Tumor Suppressor Gene at Human Chromosome 18q21.1", Science 271:350–353.
Hermann et al., 1995, "snRNP Sm Proteins Share Two Evolutionarily Conserved Sequence Motifs Which are Involved in Sm Protein–Protein Interactions", EMBO J. 14:2076–2088.
Huang et al., 1996, "Deletion and Mutation Analyses of the P16/MTS–1 Tumor Suppressor Gene in Human Ductal Pancreatic Cancer Reveals a Higher Frequency of Abnormalities in Tumor–Derived Cell Lines than in Primary Ductal Adenocarcinomas", Cancer Res. 56:1137–1141.
Kozarsky and Wilson, 1993, "Gene Therapy: Adenovirus Vectors", Curr. Opin. Genetics and Development 3:499–503.
Minvielle–Sebastia et al., 1997, "The Major Yeast Poly-(A)–Binding Protein is Associated with Cleavage Factor IA and Functions in Premessenger RNA 3'–End Formation", Proc. Natl. Acad. Sci. USA 94:7897–7902.
Morgan and Anderson, 1993, "Human Gene Therapy", Annu. Rev. Biochem. 62:191–217.
Parker et al., 1996, "Cancer Statistics", CA Cancer J. for Clinicians 46:5–27.
Qi et al., 1994, "Molecular Analysis of Pancreatic Cancer: Isolation of cDNA for Differentially Expressed Genes by Subtraction Hybridization and mRNA Display Techniques", Adv. Gene Technology: Proc. 1994 Miami Bio/Technology Winter Symposium 4:18.
Redston et al., 1994, "p53 Mutations in Pancreatic Carcinoma and Evidence of Common Involvement of Homocopolymer Tracts in DNA Microdeletions", Cancer Res. 54:3025–3033.
Schweinfest et al., 1997, "CaSm: An Sm–Like Protein that Contributes to the Transformed State in Cancer Cells", Cancer Res. 57:2961–2965.
Schweinfest et al., 1993, "Identification of a Colon Mucosa Gene that is Down–Regulated in Colon Adenomas and Adenocarcinomas", Proc. Natl. Acad. Sci. USA 90:4166–4170.
Schweinfest et al., 1990, "Subtraction Hybridization cDNA Libraries from Colon Carcinoma and Hepatic Cancer", Genet Anal. Techn. Appl: 7:64–70.

(List continued on next page.)

*Primary Examiner*—Gabriele Bugaisky
(74) *Attorney, Agent, or Firm*—Pennie & Edmonds LLP

(57) ABSTRACT

The present invention relates to a novel gene, CaSm, that is highly expressed in cancer tissues and cell lines, especially pancreatic cancer. The full length cDNA of CaSm encodes a protein of 133 amino acids. CaSm contains the two Sm motifs found in the common snRNP proteins, with the greatest homology to the Sm G protein (60% similarity). The present invention further encompasses CaSm peptides, fusion proteins, host cell expression systems, antibodies to CaSm, antisense CaSM molecules, and compounds that modulate CaSm gene expression or CaSm activity. Antisense CaSm RNA is able to alter the transformed phenotype of pancreatic cancer cells by reducing their ability to form large colonies in soft agar when compared to untransfected cells. The present invention also encompasses methods for disease diagnosis, drug screening and the treatment of cancer.

1 Claim, 9 Drawing Sheets

PUBLICATIONS

Figure 1:
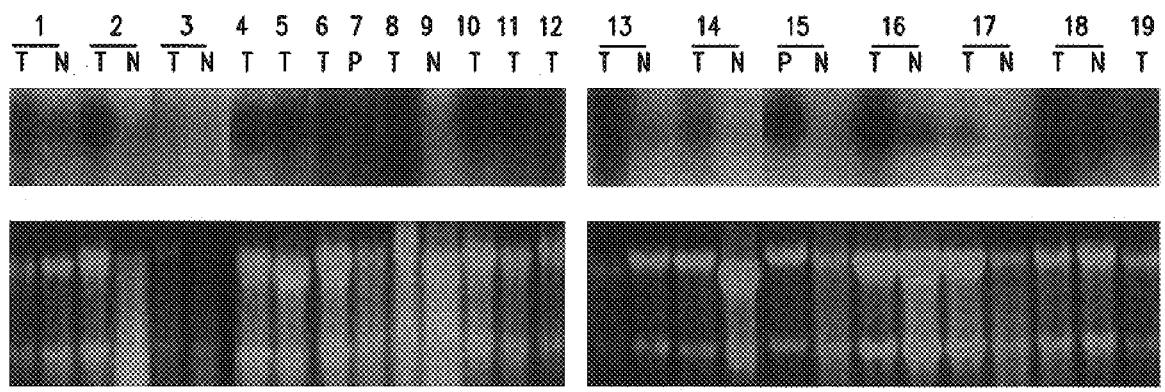

Seraphin, 1995, "Sm and Sm–like Proteins Belong to a Large Family: Identificatioin of Proteins of the U6 as well as the U1, U2, U4 and U5 snRNPs", EMBO J. 14:2089–2098.

Tada et al., 1996, "Analysis of K–ras Gene Mutation in Hyperplastic Duct Cells of the Pancreas without Pancreatic Disease", Gastroenterol. 110:227–231.

Tarun et al., 1997, "Translation Initiation Factor eIF4G Mediates in vitro Poly(A) Tail–Dependent Translation", Proc. Natl. Acad. Sci. 94:9046–9051.

Tarun and Sachs, 1996, "Association of the Yeast Poly(A) Tail Binding Protein with Translation Initiation Factor eIF–4G", EMBO J. 15:7168–7177.

Wagner, 1994, "Gene Inhibition Using Antisense Oligonucleotides", Nature 372:333–335.

Woppmann et al., 1990, "Characterisation of Human and Murine snRNP Proteins by Two–Dimensional Gel Electrophoresis and Phosphopeptide Analysis of U1–SPecific 70K Protein Variants", Nucl. Acids Res. 18:4427–4438.

* cited by examiner

```
                                    Sm motif 1                              Sm motif 2
CaSm    MNYMPGTASLIEDIDKK HLVLLRDGRTLIGFLRSIDQFANLVLHQTVER IHVGKKYGDIP RGIFVVRGENVVLL GEIDLE
                        .: ...|  . :|||  : |..|| : |:||::|.|:|||:..:.||  : |...  |:.|:||:.:::  ....:
Sm G   -MSKAHPPELKKFMDKK LSLKLNGGRHVQGILRGFDPFMNLVIDECVEM ATSGQQNN... IGMVVIRGNSIIML EALERV CORE                    V------G----G----FD--MN--L----E                 LG-V-IRG-NI---
                        U-U-------U---U--U---U-Z-U--Z--Z                U--UZU----U-ZU
                        1                              32               1             14

CaSm    KESDTPLQQVSIEEILEEQRVEQQTKLEAEKLKVQALKDRGLSIPRADTLDEY
```

FIG. 3A

```
                                     Sm motif 1                              Sm motif 2
CaSm       3 ◊YMPGTASLIEDIDKK HLVLLRDGRTLIGFLRSIDQFANLVLHQTVER IHVGKKYGDIP RGIFVVRGENVVLL
              |:||.:||:|:::|||  ||:|||||.|||||||||||||:|.:.|||.  |:| :::...|:::|||||  |
C.elegans  7 ◊YLPGAISLFEQLDKK LLVVLRDGRKLIGFLRSIDQFANLILEDVVERT FVEKYFCETG QGFMLIRGENVELA CaSm       GEIDLEKESDTPLQQVSIEEILEEQRVEQQ..TKLEAEKLKVQALKDRG◊ 121
           ||||  .. :|.| ||| ||: .|:|:: .| .:. || ||  |. :
C.elegans  GEID..DTIETGLTQVSPEEF...RRLEDEYIAKNPPKFLKRQAEKTEE◊ 122
```

FIG. 3B

```
                                    Sm motif 1                              Sm motif 2
CaSm     4 ◊MPGTASLIEDIDKK HLVLLRDGRTLIGFLRSIDQFANLVLHQTVER IHVG..KKYGDIP RGIFVVRGENVVLL
            :...||.::::.|:| :|||||||| |:.||..:|: |||:|::.|||..: .||::.|||||::||||||:|
Yeast   40 ◊FTTTAAIVSSVDRK IFVLLRDGEMLFGVLRTFDQYANLILQDCVER IYFSEENKYAEED RGIFMIRGENVVML CaSm     GEIDLEKESDT..PLQQVSIEEILEEQRVEQQTKLEAEKLKVQALKDRGL...SIPRADTL◊ 130
         ||:||::||.:. :::::...|:: ... :::::..|. |..: :|: ....| .
Yeast    GEVDIDKEDQPLEAMERIPFKEAWLTKQKNDEKRFKEETHKGKKMARHGIVYDFHKSDMY 172
```

FIG. 3C

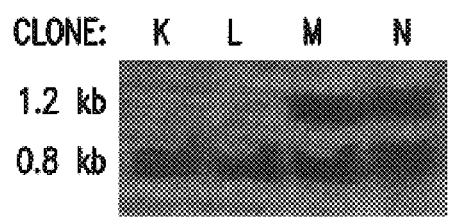
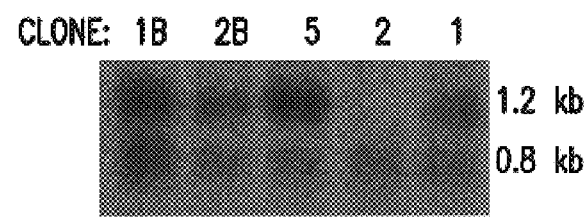
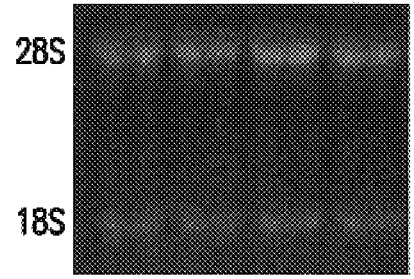
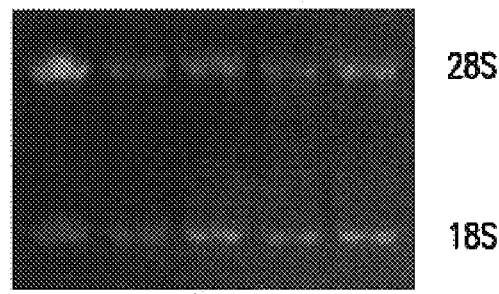
FIG.4A    FIG.4B

Clone K

Panc-1

Clone L

Clone 1

Clone 2

```
    cttccggcaggcccgccggcgatgaaagccggggcagaagtgctgtgtctccggtctcgtggattcccggcttggtcccaccgagcggcggcgactgcggtagga
1   ----+----+----+----+----+----+----+----+----+----+----+----+----+----+----+----+----+----+----+----+   100
    gaaggccgtccggggcgccgccgacttttcggcccgctcttcacgaccagagccagctcctaaggcccaaccaggtggctccgcctgacgccatccct gggaactggttttgacgcgctggcgctccccgcctgtgcattgcagcattatttcagttcaaaATGAACTATATGCCTGGCACCGCCAGCCTCATCGAG
101 ----+----+----+----+----+----+----+----+----+----+----+----+----+----+----+----+----+----+----+----+   200
    cccttgaccaaaactgcgaccgacgcgaggcggcgacacgtaacgtcgataaagtcaagttttacttgatatacgaccgtggcggtcggagtagtc
                                                           M  N  Y  M  P  G  T  A  S  L  I  E GACATTGACAAAAAGCACTTGGTTCTGCTTCGAGATGGAAGGACACTTATAGGCTTTTTAAGGAAGCATTGATCAATTTGCAAACTTAGTGCTACATCAGA
201 ----+----+----+----+----+----+----+----+----+----+----+----+----+----+----+----+----+----+----+----+   300
    ctgtaactgttttttcgtgaaccagacgaagctcttacctacctccttcctgtgaatatccgaaaattcttcgtaactagttaaacgtttgaatcacgatgtagtct
    D  I  D  K  K  H  L  V  L  L  R  D  G  R  T  L  I  G  F  L  R  S  I  D  Q  F  A  N  L  V  L  H  Q  T CTGTGGAGCGTATTCATGTGGGCAAAAAATACGGTGATATTCCTCGAGGGATTTTTGTGGTCCAGGGGAGAAAATGTGGTCCTACTAGGAGAGAAATAGACTT
301 ----+----+----+----+----+----+----+----+----+----+----+----+----+----+----+----+----+----+----+----+   400
    gacacctcgcataagtacacccgttttttatgccactataaggagctccctaaaaacaccagtcccctcttttaccaccaggatgatccctctttatctgaa
    V  E  R  I  H  V  G  K  K  Y  G  D  I  P  R  G  I  F  V  V  R  G  E  N  V  V  L  L  G  E  I  D  L GGAAAAGGAGAGTGACACACCCCTCCAGCAAGTATCCATTCCATTGAAGAAATTCTAGAAGAACAAAGGGTGGAACAGCAGACCAAGCTGGAAGCAGAGAAGTTG
401 ----+----+----+----+----+----+----+----+----+----+----+----+----+----+----+----+----+----+----+----+   500
    cctttttcctcactgtgtggggagtcgttcatagtaacttcttaagatcttcttgttccacctttgtcgtcctttgcgtcggacttcgtcttcttcaac
    E  K  E  S  D  T  P  L  Q  Q  V  S  I  E  E  I  L  E  E  Q  R  V  E  Q  Q  T  K  L  E  A  E  K  L AAAGTGCAGGCCCTGAAGGACCGAGGTCTTTCCATTCCTCGAGCAGATACTCTTGATGAGTACTAAtcttttgcccagaggctgttggctcttgaagagt
501 ----+----+----+----+----+----+----+----+----+----+----+----+----+----+----+----+----+----+----+----+   600
    tttcacgtccggactttcctggctccgggaaagtaaggagctcgtcatgagaactactactcatgattagaaacggtcctccgacaaccgagaacttctca
    K  V  Q  A  L  K  D  R  G  L  S  I  P  R  A  D  T  L  D  E  Y  *
```

FIG.6A

```
     agggctgtcactgagtgaaagtgacatcctgcccacctcacgcattgatcacagactgtagagttttgaaagtcacttttatttttaattattttac
601  ····+····:····+····:····+····:····+····:····+····:····+····:····+····:····+····:····+····:····+  700
     tccccgacagtgactcacttctactgtaggaccggtggagtgcgtaaactagtgtctgacatctcaaaactttcagtgaaataaaattaataaaatg atatgcaacatgaagaaatcgtgtagtgggttttttttttaaataacaaaatcactgttaaagaaacagtggcatagactcctcacacatcactgtg
701  ····+····:····+····:····+····:····+····:····+····:····+····:····+····:····+····:····+····:····+  800
     tatacgttgtacttcttagcacatccaccaaaaaaaattattgtttagtgacaaattctttgtcaccgtatctgaggaagtgtgtagtgacac gcaccagcaactacttctttatattgttcttcatatcccaaattagagtttacagggacagtcttcattactgtaaataaaatatgaatctc
801  ····+····:····+····:····+····:····+····:····+····:····+····:····+····:····+····:····+·····    894
     cgtggtcgttgatgaagaatataacaagaagtatagggtttaatctcaaatgtccctgtcagaagtaaatgaacattattttatacttagag
```

FIG.6B

METHODS AND COMPOSITIONS FOR DIAGNOSIS AND TREATMENT OF CANCER

This application claims the benefit of Provisional application Ser. No. 60/039,980, filed Mar. 4, 1997.

1. INTRODUCTION

The present invention relates to the discovery, identification and characterization of nucleic acid molecules that encode CaSm, a novel protein that is overexpressed in various cancer tissues. The invention encompasses CaSm nucleotides, host cell expression systems, CaSm proteins, fusion proteins, polypeptides and peptides, antibodies to the gene product, antisense CaSm nucleic acids, transgenic animals that express an CaSm transgene, or recombinant knock-out animals that do not express the CaSm, and other compounds that modulate CaSm gene expression or CaSm activity that can be used for diagnosis, disease monitoring, drug screening, and/or the treatment of cancer disorders, including but not limited to cancer.

2. BACKGROUND

2.1 Cancer

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Pre-malignant abnormal cell growth is exemplified by hyperplasia, metaplasia, or most particularly, dysplasia (for review of such abnormal growth conditions, see Robbins & Angell, 1976, Basic Pathology, 2d Ed., W. B. Saunders Co., Philadelphia, pp. 68–79.) The neoplastic lesion may evolve clonally and develop an increasing capacity for growth, metastasis, and heterogeneity, especially under conditions in which the neoplastic cells escape the host's immune surveillance (Roitt, I., Brostoff, J and Kale, D., 1993, Immunology, 3rd ed., Mosby, St. Louis, pps. 17.1–17.12). Clinical data and molecular biologic studies indicate that cancer is a multi-step process that begins with minor pre-neoplastic changes, which may under certain conditions progress to neoplasia.

Screening is the search for disease in asymptomatic people. Once an individual has a positive screening test, or signs or symptoms have been identified, further diagnostic tests are performed to determine the best course of treatment. The benefit of early detection mainly derives from the opportunity to treat disease before it has spread, when cure or control is most achievable. The American Cancer Society recommends regular cancer-related checkups for asymptomatic and at-risk individuals which include examination for cancers of the breast, colon, skin, and prostate, etc.

As understanding of the pathophysiological role of cancer increases, the role of both tumor markers and genetic information becomes more important in the management and treatment of cancer patients. Tumor markers are substances that can be measured quantitatively by biochemical or immunochemical means in tissue or body fluids to detect a cancer, to establish the extent of tumor burden before treatment, to diagnose as aides in staging or confirmation of histopathology, to predict the outcome of drug therapy, and to monitor relapse. Measurement of tumor markers have been used on screening total populations as well as in testings of high-risk groups.

Aberrant regulation of the mechanisms that control cell growth and differentiation results in cellular transformation. Molecular analysis has demonstrated that multiple mutations in oncogenies and tumor suppressor genes are required to manifest the malignant phenotype. This multi-step process is well illustrated by colorectal cancers, which typically develop over decades, and appear to require at least seven genetic events for completion (Kinzler et al., 1996, Cell, 87:159–170). Knowledge of the genetic bases of cancer has important clinical implications, the most immediate of which is improved diagnosis through genetic testing.

For example, the recent discoveries that individuals with BRCA1 and BRCA2 mutations have a predisposition to cancer may now facilitate the detection of an early onset type disease for hereditary breast cancer (Easton et al., 1993, Cancer Surv, 18:95–1131; Miki et al., 1994, Science, 266:66–71; Tavtigian et al., 1994, Nature Gen, 12:333–337). However, the incidence of these cases is just 5–10% of all known breast cancers (Easton et al., 1993, Cancer Surv, 18:95–1131; Miki et al., 1994, Science, 266:66–71; Tavtigian et al., 1994, Nature Gen, 12:333–337). Thus, early and late stage specific tumor markers are still needed for more than 90% of sporadic forms of breast malignancies.

Colorectal and breast cancers are just examples of a handful of malignant diseases which have been studied extensively at a molecular and genetic level. But there remains a large number of cancers, which awaits molecular biological characterization. The identification of tumor markers and tumor genes associated with these cancers will greatly assist in screening and identifying individuals at risk for the malignant diseases, and aid the search for novel therapeutic modalities.

2.2 Pancreatic Cancer

Pancreatic cancer is a disease of the industrialized world, for example, the incidence in Japan has risen from 1.8 per 100,000 in 1960 to 5.2 per 100,000 in 1985. Cigarette smoking and a high fat diet have been associated with the development of the disease. (Beazley et al., 1995, Chapter 15 in Clinical Oncology, 2nd edition, ed. by Murphy et al., American Cancer Society). Ductal adenocarcinoma of the exocrine pancreas is the most common pancreatic tumor type and is the fourth leading cause of cancer deaths in the United States (Parker et al., 1996, CA-A Cancer Journal for Clinicians, 46:5–27). Cancer of the pancreas is highly malignant. Most patients are diagnosed at an advanced stage beyond the scope of potentially curative treatment (pancreatic cancer has an extremely poor prognosis with the five year survival of less than 3%; Warshaw et al., 1992, N. Engl. J. Med., 326:455–465). Distant metastases, particularly to liver, occur early in the course of the disease. Median survival after diagnosis is 6 months. An increased incidence of pancreatic carcinoma occurs among patients with chronic pancreatitis. The clinical diagnosis of pancreatic cancer is frequently made late in the course of the disease. The initial diagnostic test of choice is computed tomography (CT) scan, followed by ultrasonography. A fine needle aspiration biopsy may be obtained by CT guidance to confirm the diagnosis. The diagnostic test may provide staging information. Generally, tumor markers have not been helpful in the diagnosis or staging of pancreatic carcinoma.

Improved survival is anticipated if pancreatic cancer can be identified and detected at an early stage. Recent surgical literature reports a higher 5-year survival (up to 20%), primarily in patients with small (<2 cm) tumors (Cameron et al., 1995, Surgical Clinics of North America, 75:939–951). Staging of pancreatic cancer is based upon the degree of metastasis, and patients presenting with early-stage disease have a much better prognosis than those presenting at a late stage. The majority of survivors are those who have small lesions and negative lymph nodes (T1, N0, M0).

Surgery with adjuvant therapy (5-fluorouracil and radiation) offers the best chance of success in treatment of pancreatic cancer, but unfortunately, a majority of the patients on presentation are ineligible. Treatment of unresectable cancer with drugs has been relatively disappointing even when combinations of multiple drugs are used. See Brennan et al., in Ch 27 "Cancer: Principles and Practice of Oncology", 4th Ed., ed. by DeVita et al., J. B. Lippincott Co., Philadelphia, 1993.

Successful treatment, therefore, is dependent upon very early diagnosis and, thus, it is important to find additional pancreatic cancer markers that may facilitate this early detection.

Although the molecular etiology of pancreatic cancer is not defined, several genetic alterations have been detected. For example, the most common changes yet recognized are mutations in the K-ras oncogeny (Almoguera et al., 1988, Cell, 53:549–554) and mutations or homozygous deletions in several tumor suppressor genes, including TP53 (Redston et al., 1994, Cancer Res., 54:3025–3033), p16/MTS-1 (Caldas, et al., 1994, Nature Genet., 8:27–32; Huang et al., 1996, Cancer Res., 56:1137–1141) and DPC4 (Hahn et al., 1996, Science, 271:350–353). In addition, gene amplification plays a role in some pancreatic cancers (Cheng et al., 1996, Proc. Natl. Acad. Sci., USA, 93:3636–3641). However, these multiple parameters remain poorly correlated with the molecular events associated with a multi-step progression of pancreatic malignancy. Thus, there is a great need for additional genetic markers which would facilitate a better understanding of the molecular biology of pancreatic cancer, and provide the information to develop novel screening and early diagnostic tests.

3. SUMMARY OF THE INVENTION

The present invention relates to the identification of novel genes whose expression pattern is unregulated in cancer tissues and cell lines, and the use of such genes and gene products as targets for diagnosis, drug screening and therapies.

In particular, the compositions of the present invention encompass nucleic acid molecules that encode the novel cancer-associated Sm-like (CaSm) protein, including recombinant DNA molecules, cloned genes or degenerate variants thereof, and naturally occurring variants which encode novel CaSm gene products. The compositions of the present invention additionally include cloning vectors, including expression vectors, containing the nucleic acid molecules of the invention, and hosts which contain such nucleic acid molecules. The compositions of the present invention also encompass the CaSm gene products, variants and fragments thereof, fusion proteins, and antibodies directed against such CaSm gene products or conserved variants or fragments thereof.

The nucleic acid sequence of the human CaSm gene (SEQ ID NO: 1) is deposited with GenBank and is given the accession number AF000177. The CaSm gene produces a transcript of approximately 1.2 kb and encodes a protein of 133 amino acids with a molecular weight of approximately 15,179 daltons. Transcripts were detected in several cancer cell lines, as well as various normal tissues, including thymus, breast, colon, kidney, pancreas and heart. The amino acid sequence of the predicted full length CaSm gene product does not contain either a recognizable signal sequence or transmembrane domain, indicating that the CaSm gene product is an intracellular protein. The amino acid sequence shares significant homology with the small nuclear ribonucleoprotein (snRNP) Sm G protein.

The present invention further relates to methods for the diagnostic evaluation and prognosis of cancer, especially pancreatic cancer. For example, nucleic acid molecules of the invention can be used as diagnostic hybridization probes or as primers for diagnostic PCR analysis for detection of abnormal expression of the CaSm gene.

Antibodies to CaSm gene product of the invention can be used in a diagnostic test to detect the presence of CaSm gene product in body fluids. In specific embodiments, measurement of CaSm gene product levels can be made to detect or stage cancer, especially pancreatic cancer.

The present invention also relates to methods for the identification of subjects having a predisposition to cancer. For example, nucleic acid molecules of the invention can be used as diagnostic hybridization probes or as primers for diagnostic PCR analysis for the identification of CaSm gene mutations, allelic variations and regulatory defects in the CaSm gene.

Further, methods and compositions are presented for the treatment of cancer, especially pancreatic cancer. Such methods and compositions are capable of modulating the level of CaSm gene expression and/or the level of CaSm gene product activity. Inhibition of CaSm expression by antisense RNA reduced the transformed phenotype of pancreatic cancer cell lines, and the tumorigenicity of cancer cells when injected into SCID mice.

Still further, the present invention relates to methods of use of the CaSm gene and/or CaSm gene products for the identification of compounds which modulate CaSm gene expression and/or the activity of CaSm gene products. Such compounds can be used as agents to prevent and/or treat cancer. Such compounds can also be used to palliate the symptoms of the disease, and control the metastatic potential of the cancer.

4. BRIEF DESCRIPTION OF THE FIGURES

FIG. 1. Expression of CaSm mRNA in pancreatic tissues. Total RNA (5 μg/lane) from surgically obtained pancreas samples was electrophoresed on 1.2% agarose containing formaldehyde, transferred to a nylon membrane and hybridized with $^{32}$P-labeled CaSm probe. T, tumor (or suspect mass); N, normal; P, pancreatitis. Bracketed samples are specimens isolated from the same patient. These pairs constitute a laneset. Otherwise, single specimens from separate individuals are shown in unpaired lanes. Laneset 1, benign mass; laneset 2, adenocarcinoma; laneset 3, adenocarcinoma lane 4, insulinoma; lane 5, adenocarcinoma metastasis to colon; lane 6, adenocarcinoma; lane 7, pancreatitis; lane 8, neoplasm with low to moderate malignant potential; lane 9, normal pancreas; lane 10, adenocarcinoma; lane 11, adenocarcinoma; lane 12, adenocarcinoma; laneset 13, adenocarcinoma; laneset 14, adenocarcinoma; laneset 15, pancreatitis; laneset 16, adenocarcinoma; laneset 17, adenocarcinoma; laneset 18, adenocarcinoma; lane 19, adenocarcinoma. The lower panels shows the ethidium bromide stained RNA.

Figure 2A:
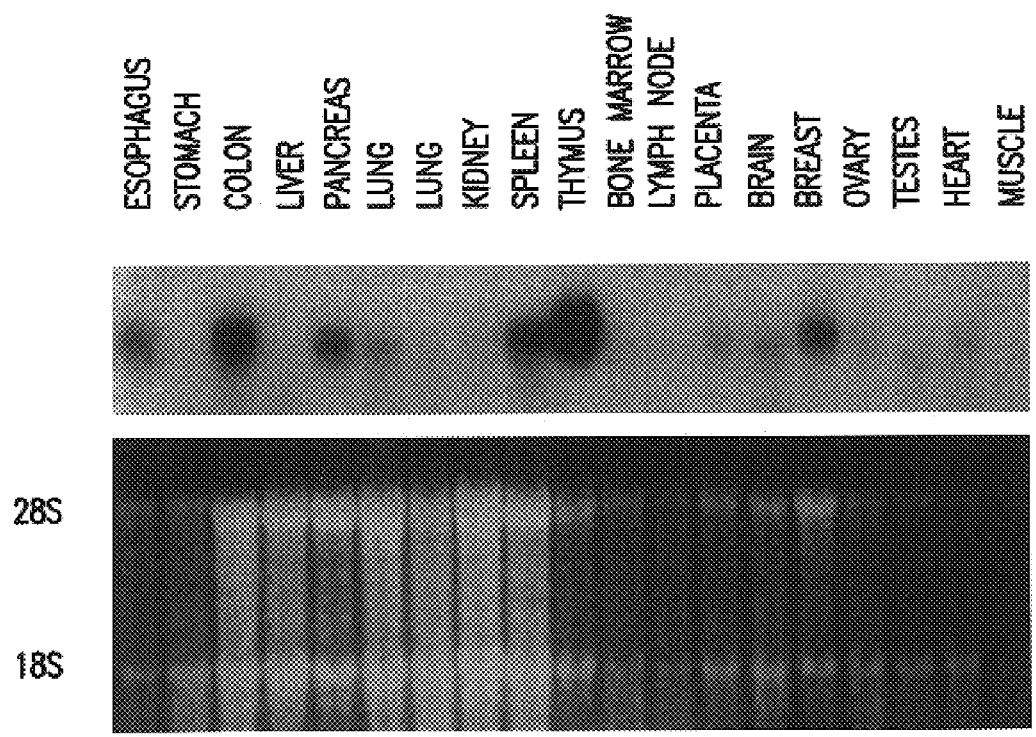
Figure 2B:
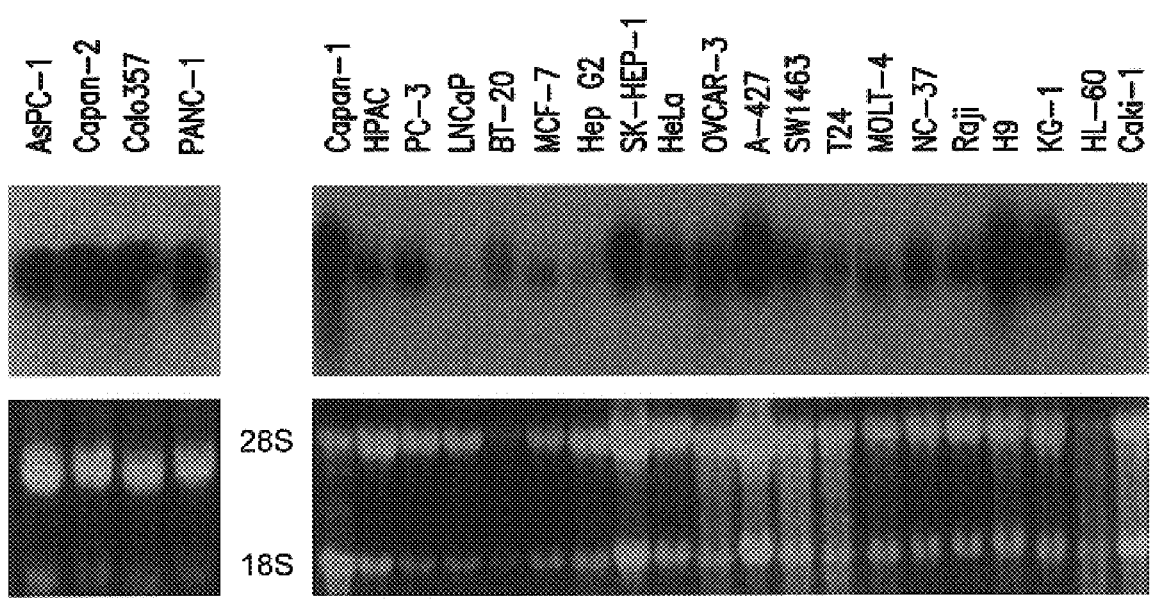

FIGS. 2A–2B. CaSm mRNA expression in human tissues and cancer cell lines. Total RNA (10 μg/lane) was electrophoresed on 1.2% agarose containing formaldehyde, transferred to a nylon membrane and hybridized with $^{32}$p-labeled CaSm probe. FIG. 2A. Shows Northern blot analysis using RNA from the indicated human tissues. FIG. 2B. Shows Northern blot analysis using RNA from the indicated cancer cell lines. The cell lines were derived from tumors originating in human pancreas (CAPAN-1, HPAC), prostate (PC-3, LNCAP), breast (BT20, MCF-7), liver (Hep G2, SKHEP-1), cervix (HeLa), ovary (OVCAR-3), lung (A-427), bladder (T24), rectum (SW1463), nonerythroid hematopoietic cells (MOLT-4, NC-37, Raji, H9, KG-1, HL-60), and kidney (Caki-1). The lower panel shows the ethidium bromide-stained RNA.

FIGS. 3A–3C. Homology of CaSm protein to Sm G protein and to hypothetical proteins. The diamond (◇) indicates that the sequence is not shown in its entirety. FIG. 3A. Shows alignment of CaSm (SEQ ID NO:1) human Sm G protein (SEQ ID NO:2). The bracketed areas denote Sm motifs 1 and 2, as indicated. The core consensus for the Sm motifs is that deduced by Hermann et al. (1995, EMBO J, 14:2076–2088). U denotes uncharged, hydrophobic amino acids (L, I, V, A, F, W, Y, C, M); Z denotes an uncharged, hydrophobic amino acid plus T or S. FIG. 3B. Shows aliagnment of CaSm protein (SEQ ID NO:3) to *Caenorhabditis elegans* gene product (SEQ ID NO:4) deduced from open reading frame J0714 (PIR S55137) in cosmid F40F8 (GenBank accession number Z69302). FIG. 3C. Shows alignment of CaSm (SEQ ID NO:5) protein to *Saccharomyces cerevisiae* gene product ORF YJL124c (SEQ ID NO:6) as encoded by DNA clone accession number Z49399.

FIGS. 4A–4B. Reduction of endogenous CaSm expression in stable antisense transfectants. RNA (5 $\mu$g/lane) from individual stable transfectants containing the CaSm antisense construct was electrophoresed on 1.5% agarose containing formaldehyde, transferred to a nylon membrane and hybridized with $^{32}$P-labeled CaSm probe. Sizes of the endogenous CaSm mRNA (1.2 kb) and the transfected antisense RNA (0.8 kb) are indicated. The lower panels show the ethidium bromide stained RNA. FIG 4A: Results for clones K, L, M and N. FIG. 4B: Results for clones 1B, 2B, 5, 2 and 1.

Figure 5A:
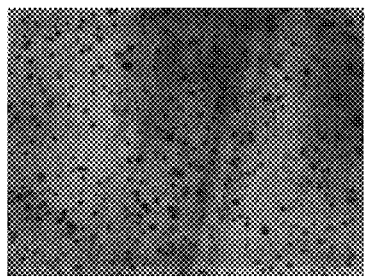
Figure 5C:
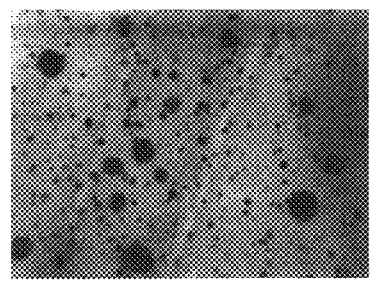
Figure 5B:
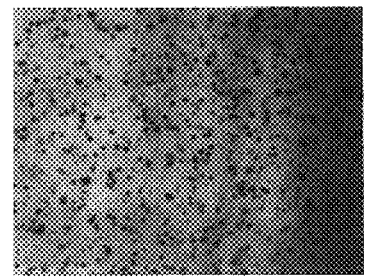
Figure 5D:
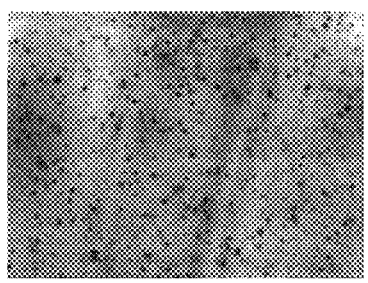
Figure 5E:
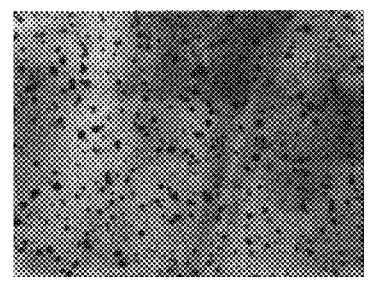
Figure 5F:
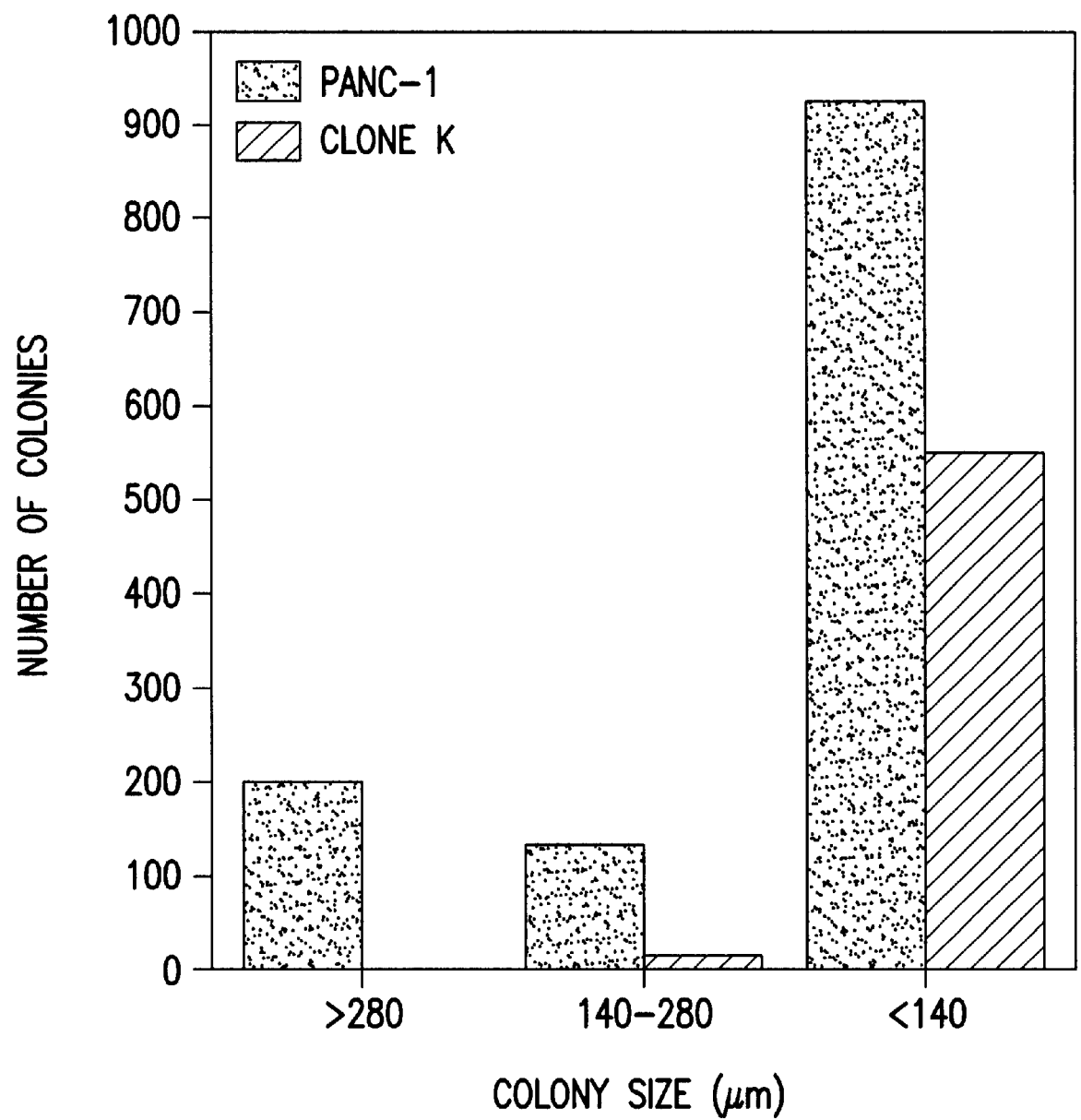

FIGS. 5A–5F. Reduction of anchorage independent growth in antisense transfectants. Soft agar colonies formed after three weeks from parental pancreatic cancer cell line PANC-1 and from 4 antisense transfectant clones are shown in FIGS. 5A–5E. FIG. 5A: Clone K. FIG. 5B: Clone L. FIG. 5C: PANC-1. FIG. 5D: Clone 1. FIG. 5E: Clone 2. FIG. 5F: Quantification of the soft agar colonies, by size, from PANC-1 and from clone K.

FIGS. 6A–6B. Nucleotide sequence and predicted amino acid sequence of CaSm. FIG. 6A: Nucleotide sequence from nucleotide position 1 to 600. FIG. 6B: Nucleotide sequence from nucleotide position 601 to 894.

DETAILED DESCRIPTION OF THE INVENTION

The present invention relates to the discovery and characterization of a nucleic acid molecule encoding a CaSm protein whose expression is elevated in cancer tissue and cell lines.

In the development of neoplasia, there are a subset of genes that will be specifically expressed at various stages, and some of these will be critical for the progression of malignancy, especially those associated with the metastatic spread of the disease. In order to identify and isolate genes whose expression is associated with pancreatic cancer in various stages of neoplastic development, the inventors undertook subtractive-hybridization cloning (Schweinfest et al., 1990, Gene Anal. Techn., 7:64–70; Schweinfest et al., 1993, Proc. Natl. Acad. Sci., 90:4166–4170). RNA was prepared from pancreatic cancer cell line CAPAN-1 and more normal pancreatic epithelial cell line HS680. PAN. Complementary cDNA clones obtained by subtractive hybridization were selected by differential hybridization with total cDNA to CAPAN-1 and HS680. PAN mRNA. One of those clones that had a much stronger hybridization signal with CAPAN-1 cDNA compared to HS680. PAN cDNA was designated as CaSm. The CaSm cDNA insert was labeled and used to probe a northern blot of tumor and normal pancreatic tissue RNAs to confirm the elevated level of expression in tumor cells. The discovery of CaSm and other differentially expressed genes will be useful for diagnosis and for monitoring disease progression, as well as for facilitating the molecular definition of specific stages of tumor development. This information will also assist in patient prognosis as well as in the selection of treatment modalities. In addition, molecular definition of new genes involved in cancers will yield novel targets for gene therapy and for therapeutic intervention.

The compositions of the invention described in the following sections are recombinant mammalian CaSm DNA molecules, cloned genes, or degenerate variants thereof. Also described herein are nucleic acid probes useful for the identification of CaSm gene mutations and the use of such nucleic acid probes in diagnosing cancer; and antisense RNA useful for the modulation of CaSm gene expression in cancer cells. The compositions of the present invention further include CaSm gene products (e.g., peptides, proteins) that are encoded by the CaSm gene. The present invention also provides antibodies against CaSm gene products, or conserved variants or fragments thereof. Such antibodies can be used to measure the level of CaSm gene products in biological fluids and tissues of a patient. Thus, the present invention also encompasses methods and kits for the diagnosis, prognosis and staging of cancer, especially pancreatic cancer, and the monitoring of the effect of a therapeutic treatment.

Further provided are methods for the use of the CaSm gene and/or CaSm gene products in the identification of compounds which modulate the expression of the CaSm gene. The CaSm gene is a novel gene of which the expression is abnormal in various cancer cell lines and tissues. As such, the CaSm gene product can be involved in the mechanisms underlying the onset and development of cancer as well as the infiltration and metastatic spread of cancer. Thus, the present invention also provides methods for the prevention and/or treatment of cancer, and for the control of metastatic spread of cancer that is based on modulation of the expression of CaSm.

5.1 The CaSm Gene

Nucleic acid sequences of the identified CaSm gene are described herein. The full-length CaSm cDNA was isolated using a partial CDNA clone (CA3-30) identified by subtractive hybridization (Schweinfest et al., 1990, Gene Anal. Techn., 7:64–70; Schweinfest et al., 1993, Proc. Natl. Acad. Sci., 90:4166–4170).

The full length cDNA clone was sequenced and found to be a novel gene consisting of 894 nucleotides including a polyadenylation signal at nucleotides 878–883 as shown in FIG. 6. The translational start signal is contained within the sequence TCAAA<u>ATG</u>A (nucleotides 160–168), which contains the requisite purines at positions −3 and +4 (Kozak et al., 1991, J. Cell Biol., 115:887–903). The largest open reading frame can encode a 133 amino acid polypeptide (nucleotides 165–563).

A deposit of the CaSm cDNA clone as a plasmid within *E. coli* strain DH5α was made at the American Type Culture Collection (ATCC), 12301 Parklawn Drive Rockville, Md. on Jul. 11, 1997, under the Accession number 98497.

As used herein, "CaSm gene" refers to (a) a gene containing the DNA sequence shown in FIG. 6 or contained in the cDNA clone in *E. coli* strain DH5α, as deposited with the American Type Culture Collection (ATCC) on Jul. 11, 1997, bearing ATCC Accession No. 98497; (b) any DNA sequence that encodes the amino acid sequence shown in FIG. 6 or encoded by the cDNA clone within *E. coli* cells as deposited with American Type Culture Collection (ATTC) on Jul. 11, 1997, bearing ATCC Accession No. 98497; (c) any DNA sequence that hybridizes to the complement of the DNA sequences that encode the amino acid sequence shown in FIG. 6 or contained in the cDNA clone in *E. coli* strain DH5α, as deposited with the American Type Culture Collection (ATCC) on Jul. 11, 1997, bearing ATCC Accession No. 98497, under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at page 2.10.3); or (d) any DNA sequence that hybridizes to the complement of the DNA sequences that encode the amino acid sequence shown in FIG. 6 or contained in the cDNA clone in *E. coli* strain DH5α, as deposited with the American Type Culture Collection (ATCC) on Jul. 11, 1997, bearing ATCC Accession No. 98497, under moderately stringent conditions, e.g., washing in 0.2×SSC/0.1% SDS at 42° C. (Ausubel et al., 1989, supra) and encodes a gene product functionally equivalent to an CaSm gene product encoded by sequences shown in FIG. 6 or contained in the cDNA clone in *E. coli* strain DH5α, as deposited with the American Type Culture Collection (ATCC) on Jul. 11, 1997, bearing ATCC Accession No. 98497.

In one embodiment of the invention, CaSm gene may also encompass fragments and degenerate variants of DNA sequences of (a) through (d), including naturally occurring variants thereof. The CaSm gene fragment may be a complementary DNA (cDNA) molecule or a genomic DNA molecule that may comprise one or more intervening sequences or introns, as well as regulating regions located beyond the 5' and 3' ends of the coding region or within an intron. One non-limiting example of a variant CaSm gene encodes a CaSm gene product in which the amino acid residues corresponding to position 22–32 of Sm motif 1 and all amino acid residues of Sm motif 2 are deleted.

A CaSm gene sequence preferably exhibits at least about 80% overall similarity at the nucleotide level to the nucleic acid sequence depicted in FIG. 6, more preferably exhibits at least about 85–90% overall similarity to the nucleic acid sequence in FIG. 6 and most preferably exhibits at least about 95% overall similarity to the nucleic acid sequence in FIG. 6.

The CaSm gene sequences of the invention are preferably of mammalian origin, and most preferably human. Mammals, include but are not limited to, mice, rats, cats, dogs, cattle, pigs, sheep, guinea pigs and rabbits.

The nucleic acid sequence of human CaSm gene (SEQ ID NO: 1) is deposited with GenBank and is given the accession number AF000177.

The invention also encompasses nucleic acid molecules encoding mutant CaSm, peptide fragments of CaSm, truncated CaSm, and CaSm fusion proteins. The gene products encoded by these nucleic acid molecules include, but are not limited to, peptides corresponding to Sm motif 1 of CaSm, Sm motif 2 of CaSm, Sm motif 1 and 2 of CaSm, or portions thereof; truncated CaSm in which the Sm motif 1 or Sm motif 2 or both is deleted; mutant CaSm in which one or more amino acid residue of CaSm, especially the ones in the Sm motif 1 or Sm motif 2, are substituted or deleted. The mutations in such CaSm mutants may occur within the core consensus for the Sm motif 1 and Sm motif 2, as shown in FIG. 3A. Examples of such mutations may occur at positions, such as but not limited to, the glycine residue at position 13 within the Sm motif 1 (amino acid residue 30 of CaSm) or the asparagine residue at position 23 within the Sm motif 1 (amino acid residue 40 of CaSm).

The CaSm gene sequences of the invention further include isolated nucleic acid molecules which hybridize under highly stringent or moderate stringent conditions to at least about 6, preferably about 12, more preferably about 18, consecutive nucleotides of the CaSm gene sequences of (a) through (d).

The invention also includes nucleic acid molecules, preferably DNA molecules, that hybridize to, and are therefore the complements of, the DNA sequences (a) through (d), in the preceding paragraph. Such hybridization conditions may be highly stringent or moderately stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as CaSm gene antisense molecules useful, for example, in CaSm gene regulation. With respect to CaSm gene regulation, such techniques can be used to modulate, for example, the phenotype and metastatic potential of cancer cells. Further, such sequences may be used as part of ribozyme and/or triple helix sequences, also useful for CaSm gene regulation.

Still further, such molecules may be used as components of diagnostic methods whereby, for example, the presence of a particular CaSm allele or alternatively spliced CaSm transcript responsible for causing or predisposing one to cancer may be detected.

Still further, the invention encompassing CaSm genes as a screen in an engineered yeast system, including, but not limited to, the yeast two hybrid system.

The invention also encompasses (a) DNA vectors that contain any of the foregoing CaSm coding sequences and/or their complements (e.g., antisense); (b) DNA expression vectors that contain any of the foregoing CaSm coding sequences operatively associated with a regulatory element that directs the transcription and/or expression of the CaSm coding sequences or antisense sequences; and (c) genetically engineered host cells that contain any of the foregoing CaSm sequences operatively associated with a regulatory element that directs the transcription and/or expression of the CaSm coding sequences or antisense sequence in the host cell. As used herein, regulatory elements include, but are not limited to inducible and non-inducible promoters, enhancers, operators and other elements known to those skilled in the art that drive and regulate expression. Such regulatory elements include but are not limited to the cytomegalovirus (hCMV) immediate early promoter, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

In addition to the CaSm gene sequences described above, homologs of such sequences, exhibiting extensive homology to the CaSm gene product present in other species can be identified and readily isolated, without undue experimentation, by molecular biological techniques well known in the art. Genes encoding CaSm homologs can be identified in microbes, such as yeast, in animals including nematodes, such as *Caenorhabditis elegans*, in vertebrates, and in mammals. Accordingly, the invention encompasses nucleotide sequences encoding CaSm homologs wherein the nucleotide sequence does not encode the *C. elegans* gene product deduced from open reading frame J0714 (PIR S55137) in cosmid F40F8 (GenBank accession number Z69302), and does not encode the *Saccharomyces cerevisiae* gene product of ORF YJL124c as in DNA clone accession number Z49399. Further, there can exist homolog genes at other genetic loci within the genome that encode proteins which have extensive homology to the CaSm gene product. These genes can also be identified via similar techniques. Still further, there can exist alternatively spliced variants of the CaSm gene.

As an example, in order to clone a mammalian CaSm gene homolog or variants using isolated human CaSm gene sequences as disclosed herein, such human CaSm gene sequences are labeled and used to screen a cDNA library constructed from mRNA obtained from appropriate cells or tissues (e.g., pancreatic epithelial cells) derived from the organism of interest. With respect to the cloning of such a mammalian CaSm homolog, a mammalian cancer cell cDNA library may, for example, be used for screening.

The hybridization and wash conditions used should be of a low stringency when the cDNA library is derived from a different type of organism than the one from which the labeled sequence was derived. Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

With respect to the cloning of a mammalian CaSm homolog, using human CaSm sequences, for example, various stringency conditions which promote DNA hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M NaHPO$_4$ (pH7.2)/1 mM EDTA/7% SDS, or hybridization in 50% formamide/0.25M NaHPO$_4$ (pH 7.2)/0.25 M NaCl/1 mM EDTA/7% SDS; followed by washing in 40 mM NaHPO$_4$ (pH 7.2)/1 mM EDTA/5% SDS at 50° C. or in 40 mM NaHPO$_4$ (pH7.2) 1 mM EDTA/1% SDS at 50° C. Both temperature and salt may be varied, or alternatively, one or the other variable may remain constant while the other is changed.

Alternatively, the labeled fragment may be used to screen a genomic DNA library of the organism of interest, again, using appropriately stringent conditions well known to those of skill in the art.

Further, a CaSm gene homolog may be isolated from nucleic acid of the organism of interest by performing polymerase chain reaction (PCR) using two degenerate oligonucleotide primer pools designed on the basis of amino acid sequences within the CaSm gene product disclosed herein. The template for the reaction may be cDNA obtained by reverse transcription of mRNA prepared from, for example, mammalian cell lines or tissue known or suspected to express a CaSm gene homology or allele.

The PCR product may be subcloned and sequenced to ensure that the amplified sequences represent the sequences of a CaSm gene nucleic acid sequence. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may be utilized to isolate full length cDNA sequences. For example, RNA may be isolated, following standard procedures, from an appropriate cellular or tissue source (e.g., one known, or suspected, to express the CaSm gene, such as, for example, pancreatic cancer cell lines). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of PCR technology and cloning strategies which may be used, see e.g., PCR Primer, 1995, Dieffenbach et al., ed., Cold Spring Harbor Laboratory Press; Sambrook et al., 1989, supra.

CaSm gene sequences may additionally be used to isolate CaSm gene alleles and mutant CaSm gene alleles. Such mutant alleles may be isolated from individuals either known or susceptible to or predisposed to have a genotype which contributes to the development of cancer, including metastasis. Mutant alleles and mutant allele products may then be utilized in the screening, therapeutic and diagnostic methods and systems described herein. Additionally, such CaSm gene sequences can be used to detect CaSm gene regulatory (e.g., promoter) defects which can affect the development and outcome of cancer.

A cDNA of a mutant CaSm gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant CaSm allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant CaSm allele to that of the normal CaSm allele, the mutation(s) responsible for the loss or alteration of function of the mutant CaSm gene product can be ascertained.

Alternatively, a genomic library can be constructed using DNA obtained from an individual suspected of or known to carry the mutant CaSm allele, or a cDNA library can be constructed using RNA from a tissue known, or suspected, to express the mutant CaSm allele. The normal CaSm gene or any suitable fragment thereof may then be labeled and used as a probe to identify the corresponding mutant CaSm allele in such libraries. Clones containing the mutant CaSm gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant CaSm allele. In this manner, gene products made from the mutant allele may be expressed and screened using standard antibody screening techniques in conjunction with antibodies raised against the normal CaSm gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In cases where a CaSm mutation results in an expressed gene product with altered function (e.g., as a result of a missense or a frameshift mutation), a set of polyclonal antibodies to CaSm gene product are likely to cross-react with the mutant CaSm gene product. Library clones detected via their reaction with such labeled antibodies can be purified and subjected to sequence analysis according to methods well known to those of skill in the art.

5.2 Protein Products of the CaSm Gene

In another embodiment, the present invention provides CaSm gene products, or peptide fragments thereof which can be used for the generation of antibodies, in diagnostic assays, or for the identification of other cellular gene products involved in the development of cancer, such as, for example, pancreatic cancer.

The amino acid sequence depicted in FIG. 6 represents a CaSm gene product. The CaSm gene product, interchangeably referred to herein as a "CaSm protein", includes mammalian CaSm gene product, and may additionally include those gene products encoded by the CaSm gene sequences described in Section 5.1, above.

In one embodiment, the CaSm gene product of the invention as depicted in FIG. 6 comprises 133 amino acids and has a predicted molecular weight of 15,179 daltons and an isoelectric point of 4.97. The amino acid sequence of the predicted full length CaSm gene product does not contain either a recognizable signal sequence or transmembrane domain, indicating that the CaSm gene product is an intracellular protein.

The 133 amino acid CaSm polypeptide shares significant homology with the snRNP Sm G protein (FIG. 3A). A computerized BESTFIT of CaSm and human Sm G protein is 32% identical and 60% similar (allowing for conservative amino acid substitutions). This similarity is nearly completely confined to the amino terminal half of CaSm (amino acids 4–78). Interestingly, this homology localizes to the two Sm motifs that characterize the Sm protein family (Hermann et al., 1995, EMBO J., 14:2076–2088). Sm motif 1 and Sm motif 2, amino acid residues 18–49 and 61–74 respectively, are responsible for protein-protein interactions, presumably necessary for the assembly of snRNP complexes (Hermann et al., 1995, EMBO J., 14:2076–2088). Most key features that constitute the Sm motifs are retained in CaSm. Specifically, the 100% conserved glycine and asparagine residues at consensus positions 13 and 23, respectively, of Sm motif 1 are also found in CaSm at amino acid positions 30 and 40 respectively. Overall, 12 of the 15 defined positions in the consensus for Sm motif 1 are conserved in CaSm. Furthermore, 10 of the 11 defined positions in the Sm motif 2 consensus are also conserved in CaSm (see FIG. 3A). A gene product of Caenorhabditis elegans and a gene product of Saccharomyces cerevisiae share even greater similarity to CaSm (72.8% and 67.7%, respectively, see FIGS. 3B and 3C). These two gene products also contain Sm motifs and are most similar to CaSm in those regions. In addition to the mammalian homologs of CaSm, these two gene products which also have a molecular weight similar to CaSm are the non-mammalian homologs of CaSm in the respective organisms. Accordingly, the invention encompasses all mammalian and non-mammalian CaSm homologs wherein the CaSm homolog is not the C. elegans gene product deduced from open reading frame J0714 (PIR S55137) in cosmid F40F8 (GenBank accession number Z69302), and is not the Saccharomyces cerevisiae gene product of ORF YJL124c as encoded by DNA clone accession number Z49399.

The predicted open reading frame (ORF) of CaSm was confirmed by its expression in an in vitro coupled transcription and translation reaction. The putative coding strand translates an 18 kilodalton polypeptide, whereas the putative non-coding strand produces a much smaller product. Moreover, only antisense probe to the putative coding strand hybridizes to mRNA taken from pancreatic cancer cells.

The CaSm gene product of the invention is associated with cellular mechanisms which regulate cell growth by post-transcriptional control of gene expression. In particular, CaSm is involved in the stimulation of translation of mRNA, and/or inhibition of messenger RNA degradation, both of which are believed to entail synergistic interactions of the polyadenylated (poly(A)) mRNA tail and the cap structure on the 5' end of an eukaryotic mRNA. Such interactions are known to be mediated by proteins that are (i) bound to the mRNA cap, e.g., the translation initiation complex, eIF-4F (which contains a large subunit, eIF4G, and in higher eukaryotes, eIF4A), which recruits the ribosome to the 5' end of the mRNA; and (ii) a poly(A) binding protein, Pab1p, which stimulates the recruitement of 40S ribosomal subunit to the mRNA when it is associated with the poly(A) tail. See Tarun et al., 1996, EMBO J 15:7168–7177; and Tarun et al., 1997, Proc. Natl. Acad. Sci. 94:9046–9051. The homologous CaSm gene product in yeast (as encoded by ORF YJL124c) is a bypass suppressor of mutations in the Pab1p gene, especially in yeast cells which contain mutations in the Pab1p and eIF-4E and eIF-4G genes. Without being bound by any theory, this observation suggests that the CaSm gene product may either perform some of the functions of Pab1p, or be active in a pathway that is parallel to the interaction between Pab1p and eIF-4G which also stimulates translation. Accordingly, the ability of the CaSm homolog to stimulate mRNA translation and rescue mutant yeast cells from lethality is consistent with the observation that overexpression of the mammalian CaSm gene product in certain cell types lead to the appearance of a transformed phenotype.

In addition, CaSm gene products may include proteins that represent functionally equivalent gene products, including all mammalian and non-mammalian CaSm gene products. Such an equivalent CaSm gene product may contain deletions, additions or substitutions of amino acid residues within the amino acid sequence encoded by the CaSm gene sequences described, above, in Section 5.1, but which result in a silent change, thus producing a functionally equivalent CaSm gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Conservative and unconservative amino acid substitution(s) within the core consensus of the Sm motifs 1 and/or 2, such as for example, the conserved glycine residue at position 13 of Sm motif 1 or the conserved asparagine residue at position 23 of Sm motif 1, are contemplated (see FIG. 3A).

"Functionally equivalent", as utilized herein, refers to a protein capable of exhibiting a substantially similar in vivo activity as the endogenous CaSm gene products encoded by the CaSm gene sequences described in Section 5.1, above. The in vivo activity of the CaSm gene product, as used herein, refers to its association with the manifestation of preneoplastic or neoplastic phenotype of a cell when present in an appropriate cell type, such as for example, pancreatic cells.

A CaSm gene product sequence preferably exhibits at least about 80% overall similarity at the amino acid level to the amino acid sequence depicted in FIG. 6, more preferably exhibits at least about 90% overall similarity to the amino acid sequence in FIG. 6 and most preferably exhibits at least about 95% overall similarity to the amino acid sequence in FIG. 6.

CaSm gene products can include peptide fragments of CaSm, truncated CaSm, and mutants thereof. These include, but are not limited to peptides corresponding to the CaSm Sm motif 1 and CaSm Sm motif 2 or portions thereof; truncated CaSm in which the Sm motif 1 or Sm motif 2 or both is deleted. Mutant CaSm peptide fragments may contain one or more conservative or unconservative amino acid substitution within the core consensus of the Sm motifs 1 and 2.

CaSm gene products can also include fusion proteins comprising a CaSm gene product sequence as described in this section operatively joined to a heterologous component. Heterologous components can include, but are not limited to sequences which facilitate isolation and purification of fusion protein (e.g., a matrix binding domain), or detectable labels. Such isolation and label components are well known to those of skill in the art. For example, a CaSm-green fluorescent protein fusion (CaSm-GFP) is expressed in a cell to facilitate localization and studies of intracellular trafficking of the CaSm protein.

The CaSm gene products or peptide fragments thereof, or fusion proteins can be used in any assay that detects or measures CaSm gene products or in the calibration and standardization of such assay.

The CaSm gene products or peptide fragments thereof, may be isolated from cellular sources, or produced by recombinant DNA technology using techniques well known in the art. Thus, methods for preparing the CaSm gene products and peptides of the invention by expressing nucleic acid containing CaSm gene sequences are described herein. Methods which are well known to those skilled in the art can be used to construct expression vectors containing CaSm gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding CaSm gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the CaSm gene coding sequences of the invention. Such host-expression systems represent vehicles by which the coding sequences of interest may be produced and subsequently recovered and/or purified, but also represent cells which may, when transformed or transfected with the appropriate nucleotide coding sequences, exhibit the CaSm gene product of the invention in situ. These include but are not limited to microorganisms such as bacteria (e.g., E. coli, B. subtilis) transformed with recombinant bacteriophage DNA, plasmid DNA or cosmid DNA expression vectors containing CaSm gene product coding sequences; yeast (e.g., Saccharomyces, Pichia) transformed with recombinant yeast expression vectors containing the CaSm gene product coding sequences; insect cell systems infected with recombinant virus expression vectors (e.g., baculovirus) containing the CaSm gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing CaSm gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the CaSm gene product being expressed. For example, when a large quantity of such a protein is to be produced, for the generation of pharmaceutical compositions comprising CaSm protein or for raising antibodies to CaSm protein, vectors which direct the expression of high levels of fusion protein products that are readily purified may be desirable. Such vectors include, but are not limited, to the E. coli expression vector pUR278 (Ruther et al., 1983, EMBO J. 2:1791), in which the CaSm gene product coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with gluta-thione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. The CaSm gene coding sequence may be cloned individually into non-essential regions (for example the polyhedrin gene) of the virus and placed under control of an AcNPV promoter (for example the polyhedrin promoter). Successful insertion of CaSm gene coding sequence will result in inactivation of the polyhedrin gene and production of non-occluded recombinant virus (i.e., virus lacking the roteinaceous coat coded for by the polyhedrin gene). These recombinant viruses are then used to infect *Spodoptera frugiperda* cells in which the inserted gene is expressed. (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the CaSm gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing CaSm gene product in infected hosts. (e.g., See Logan & Shenk, 1984, Proc. Natl. Acad. Sci. USA 81:3655–3659).

In a specific embodiment, a retroviral vector that contains the CaSm gene is used. For example, see Miller et al., 1993, Meth. Enzymol. 217:581–599. These retroviral vectors have been modified to delete retroviral sequences that are not necessary for packaging of the viral genome and integration into host cell DNA. The CaSm gene to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdrl gene to hematopoietic stem cells in order to make the stem cells more resistant to chemotherapy. Other references illustrating the use of retroviral vectors are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Specific initiation signals may also be required for efficient translation of inserted CaSm gene product coding sequences. These signals include the ATG initiation codon and adjacent sequences. In cases where an entire CaSm gene, including its own initiation codon and adjacent sequences, is inserted into the appropriate expression vector, no additional translational control signals may be needed. However, in cases where only a portion of the CaSm gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, and in particular, cancer cell lines such as, for example, CAPAN-1, CAPAN-2, ASPC-1, PANC-1 and HPAC, and normal pancreatic cell lines, such as for example, HS680.PAN.

For long-term, high-yield production of recombinant proteins, stable expression is preferred. For example, cell lines which stably express the CaSm gene product may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the CaSm gene product. Such engineered cell lines may be particularly useful in screening and evaluation of compounds that affect the endogenous activity of the CaSm gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the open reading frame of the gene is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

The CaSm gene products can also be expressed in transgenic animals. Animals of any species, including, but not limited to, mice, rats, rabbits, guinea pigs, sheep, pigs, micro-pigs, goats, and non-human primates, e.g., baboons, monkeys, and chimpanzees may be used to generate CaSm transgenic animals. The non-mammalian homologs of CaSm can also be expressed in transgenic organisms, including but not limited to, *Caenorhabditis elegans* and *Saccharomyces cerevisiae*.

Any technique known in the art may be used to introduce the CaSm transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the CaSm transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the CaSm gene transgene be integrated into the chromosomal site of the endogenous CaSm gene, gene targeting is preferred. Briefly, when such a technique is to be utilized, vectors containing some nucleotide sequences homologous to the endogenous CaSm gene are designed for the purpose of integrating, via homologous recombination with chromosomal sequences, into and disrupting the function of the nucleotide sequence of the endogenous CaSm gene. The transgene may also be selectively introduced into a particular cell type, thus inactivating the endogenous CaSm gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

Methods for the production of single-copy transgenic animals with chosen sites of integration are also well known to those of skill in the art. See, for example, Bronson et al., 1996, Proc. Natl. Acad. Sci. USA 93:9067–9072), which is incorporated herein by reference in its entirety.

Once transgenic animals or transgenic organisms have been generated, the expression of the recombinant CaSm gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals or organisms may also be assessed using techniques which include but are not limited to Northern blot analysis of tissue samples obtained from the animal or organism, in situ hybridization analysis, and RT-PCR. Samples of CaSm gene-expressing tissue, may also be evaluated immunocytochemically using antibodies specific for the CaSm transgene product.

5.3 Antibodies to CaSm Gene Products

In another embodiment, the present invention encompasses antibodies or fragments thereof capable of specifically recognizing one or more epitopes of the CaSm gene products, epitopes of conserved variants of the CaSm gene products, epitopes of mutant CaSm gene products, or peptide fragments of the CaSm gene products. Such antibodies may include, but are not limited to, polyclonal antibodies, monoclonal antibodies (mAbs), humanized or chimeric antibodies, single chain antibodies, Fab fragments, F(ab')$_2$ fragments, Fv fragments, fragments produced by a Fab expression library, anti-idiotypic (anti-Id) antibodies, and epitope-binding fragments of any of the above.

Such antibodies may be used, for example, in the detection of a CaSm gene product in an biological sample and may, therefore, be utilized as part of a diagnostic or prognostic technique whereby patients may be tested for abnormal levels of CaSm gene products, and/or for the presence of abnormal forms of the such gene products. Such antibodies may also be included as a reagent in a kit for use in a diagnostic or prognostic technique. Such antibodies may also be utilized in conjunction with, for example, compound screening schemes, as described, below, in Section 5.4.2, for the evaluation of the effect of test compounds on CaSm gene product levels and/or activity. Additionally, such antibodies can be used in conjunction with the gene therapy techniques described, below, in Section 5.4.3, to, for example, evaluate the normal and/or engineered CaSm-expressing cells prior to their introduction into the patient.

Antibodies to anti-CaSm gene product may additionally be used in a method for the inhibition of abnormal CaSm gene product activity. Thus, such antibodies may, therefore, be utilized as part of cancer treatment methods.

Described herein are methods for the production of antibodies of such antibodies or fragments thereof. Any of such antibodies or fragments thereof may be produced by standard immunological methods or by recombinant expression of nucleic acid molecules encoding the antibody or fragments thereof in an appropriate host organism.

For the production of antibodies against a CaSm gene product, various host animals may be immunized by injection with a CaSm gene product, or a fragment thereof. Fragments of CaSm can be synthesized as antigenic peptides in accordance with the known amino acid sequence of CaSm. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a CaSm gene product, or an antigenic functional derivative thereof. For example, polyclonal antibodies have been raised against synthetic peptides having the amino acid sequence of CaSm protein at amino acid residues 79–89, and at 115–133. For the production of polyclonal antibodies, host animals such as those described above, may be immunized by injection with CaSm gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against CaSm gene products. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., 1988, Science 242:1038–1041).

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.4 Uses of the CaSm Gene, Gene Products, and Antibodies

In various embodiments, the present invention provides various uses of the CaSm gene, the CaSm gene product including peptide fragments thereof, and of antibodies directed against the CaSm gene product and peptide fragments thereof. Such uses include, for example, prognostic and diagnostic evaluation of cancer, and the identification of subjects with a predisposition to a cancer, as described, below.

In one embodiment, the present invention provides a variety of methods for the diagnostic and prognostic evaluation of cancer. Such methods may, for example, utilize reagents such as the CaSm gene nucleotide sequences described in Sections 5.1, and antibodies directed against CaSm gene products, including peptide fragments thereof, as described, above, in Section 5.2.

Specifically, such reagents may be used, for example, for: (1) the detection of the presence of CaSm gene mutations, or the detection of either over- or under-expression of CaSm gene mRNA preneoplastic or neoplastic relative to normal cells, or the qualitative or quantitative detection of other alleic forms of CaSm transcripts which may correlate with cancer or susceptibility toward neoplastic changes, and (2) the detection of an over-abundance of CaSm gene product relative to the non-disease state or the presence of a modified (e.g., less than full length) CaSm gene product which correlates with a neoplastic state or a progression toward neoplasia or metastasis.

The methods described herein may be applied to samples of cells or cellular materials taken directly from a patient. Any method known in the art for collection or isolation of the desired cells or materials can be used. In particular, for pancreatic cancer, samples for testing may be obtained by techniques known in the art, such as endoscopic retrograde cholangiopancreatography (ERCP) to obtain pure pancreatic juice, or percutaneous fine needle aspiration biopsy with endoscopic ultrasonography.

The methods described herein may be performed, for example, by utilizing pre-packaged diagnostic test kits comprising at least one specific CaSm gene nucleic acid or anti-CaSm gene antibody reagent described herein, which may be conveniently used, e.g., in clinical settings or in home settings, to diagnose patients exhibiting preneoplastic or neoplastic abnormalities, and to screen and identify those individuals exhibiting a predisposition to such neoplastic changes.

The present invention is useful for the diagnosis and prognosis of malignant diseases in which the CaSm gene or gene product is implicated or is suspected to be implicated. Such malignancies include but are not limited to cancer of the pancreas, liver, ovary, lung, bladder, kidney, colon, rectum, prostate gland and cervix, and mesothelioma. Nucleic acid-based detection techniques are described, below, in Section 5.4.1. Peptide detection techniques are described, below, in Section 5.4.2.

5.4.1 Detection of CaSm Gene Nucleic Acid Molecules

Mutations or polymorphisms within the CaSm gene can be detected by utilizing a number of techniques. Nucleic acid from any nucleated cell can be used as the starting point for such assay techniques, and may be isolated according to standard nucleic acid preparation procedures which are well known to those of skill in the art. For the detection of CaSm mutations, any nucleated cell can be used as a starting source for genomic nucleic acid. For the detection of CaSm transcripts or CaSm gene products, any cell type or tissue in which the CaSm gene is expressed, such as, for example, pancreatic cancer cells, including metastases, may be utilized.

Genomic DNA may be used in hybridization or amplification assays of biological samples to detect abnormalities involving CaSm gene structure, including point mutations, insertions, deletions and chromosomal rearrangements. Such assays may include, but are not limited to, direct sequencing (Wong, C. et al., 1987, Nature 330:384–386), single stranded conformational polymorphism analyses (SSCP; Orita, M. et al., 1989, Proc. Natl. Acad. Sci. USA 86:2766–2770), heteroduplex analysis (Keen et al., 1991, Genomics 11:199–205; Perry, D. J. & Carrell, R. W., 1992), denaturing gradient gel electrophoresis (DGGE; Myers, R. M. et al., 1985, Nucl. Acids Res. 13:3131–3145), chemical mismatch cleavage (Cotton et al., 1988, Proc. Natl. Acad. Sci. USA 85:4397–4401) and oligonucleotide hybridization (Wallace et al., 1981, Nucl. Acids Res. 9:879–894; Lipshutz et al., 1995, Biotechniques 19:442–447).

Diagnostic methods for the detection of CaSm gene specific nucleic acid molecules, in patient samples (such as pancreatic juice or serum) or other appropriate cell sources, may involve the amplification of specific gene sequences, e.g., by the polymerase chain reaction (PCR; see Mullis, K. B., 1987, U.S. Pat. No. 4,683,202), followed by the analysis of the amplified molecules using techniques well known to those of skill in the art, such as, for example, those listed above. Utilizing analysis techniques such as these, the amplified sequences can be compared to those which would be expected if the nucleic acid being amplified contained only normal copies of the CaSm gene in order to determine whether a CaSm gene mutation exists.

Further, well-known genotyping techniques can be performed to type polymorphisms that are in close proximity to mutations in the CaSm gene itself. These polymorphisms can be used to identify individuals in families likely to carry mutations. If a polymorphism exhibits linkage disequilibrium with mutations in the CaSm gene, it can also be used to identify individuals in the general population likely to carry mutations. Polymorphisms that can be used in this way include restriction fragment length polymorphisms (RFLPs), which involve sequence variations in restriction enzyme target sequences, single-base polymorphisms and simple sequence repeat polymorphisms (SSLPs).

For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the CaSm gene, and the diagnosis of diseases and disorders related to CaSm mutations.

Also, Caskey et al. (U.S. Pat. No. 5,364,759, which is incorporated herein by reference in its entirety) describes a DNA profiling assay for detecting short tri and tetra nucleotide repeat sequences. The process includes extracting the DNA of interest, such as the CaSm gene, amplifying the extracted DNA, and labelling the repeat sequences to form a genotypic map of the individual's DNA.

A CaSm probe could additionally be used to directly identify RFLPs. Additionally, a CaSm probe or primers derived from the CaSm sequence could be used to isolate genomic clones such as YACs, BACs, PACs, cosmids, phage or plasmids. The DNA contained in these clones can be screened for single-base polymorphisms or simple sequence length polymorphisms (SSLPs) using standard hybridization or sequencing procedures.

Alternative diagnostic methods for the detection of CaSm gene-specific mutations or polymorphisms can include hybridization techniques which involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the CaSm gene. Preferably, the lengths of these nucleic acid reagents are at least 15 to 30 nucleotides. After incubation, all non-annealed nucleic acids are removed from the nucleic acid:CaSm molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtitre plate or polystyrene beads. In this case, after incubation, non-annealed, labeled nucleic acid reagents of the type described in Section 5.1 are easily removed. Detection of the remaining, annealed, labeled CaSm nucleic acid reagents is accomplished using standard techniques well-known to those in the art. The CaSm gene sequences to which the nucleic acid reagents have annealed can be compared to the annealing pattern expected from a normal CaSm gene sequence in order to determine whether a CaSm gene mutation is present.

Quantitative and qualitative aspects of CaSm gene expression can also be assayed. For example, RNA from a cell type or tissue known, or suspected, to express the CaSm gene, such as pancreatic cancer cells, including metastases, may be isolated and tested utilizing hybridization or PCR techniques as described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the CaSm gene. Such analyses may reveal both quantitative and qualitative aspects of the expression pattern of the CaSm gene, including activation or inactivation of CaSm gene expression and presence of alternatively spliced CaSm transcripts, for example, a splice variant of CaSm which eliminates amino acid residues 39–75 of CaSm (which corresponds to the last 11 amino acids of Sm motif 1 and all of Sm motif 2).

In one embodiment of such a detection scheme, a cDNA molecule is synthesized from an RNA molecule of interest by reverse transcription. All or part of the resulting cDNA is then used as the template for a nucleic acid amplification reaction, such as a PCR or the like. The nucleic acid reagents used as synthesis initiation reagents (e.g., primers) in the reverse transcription and nucleic acid amplification steps of this method are chosen from among the CaSm gene nucleic acid reagents described in Section 5.1. The preferred lengths of such nucleic acid reagents are at least 9–30 nucleotides.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Such RT-PCR techniques can be utilized to detect differences in CaSm transcript size which may be due to normal or abnormal alternative splicing. Additionally, such techniques can be performed using standard techniques to detect quantitative differences between levels of full length and/or alternatively spliced CaSm transcripts detected in normal individuals relative to those individuals having cancer or exhibiting a predisposition toward neoplastic changes.

In the case where detection of specific alternatively spliced species is desired, appropriate primers and/or hybridization probes can be used, such that, in the absence of such sequence, no amplification would occur. Alternatively, primer pairs may be chosen utilizing the sequence data depicted in FIG. 6 to choose primers which will yield fragments of differing size depending on whether a particular exon is present or absent from the transcript CaSm transcript being utilized.

As an alternative to amplification techniques, standard Northern analyses can be performed if a sufficient quantity of the appropriate cells can be obtained. Utilizing such techniques, quantitative as well as size related differences between CaSm transcripts can also be detected.

Additionally, it is possible to perform such CaSm gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, N.Y.).

The results obtained by the methods described herein may be combined with diagnostic test results based on other genes that are also implicated in the pathology of the cancer. For example, in pancreatic cancer, K-ras mutations have been observed in patients 18 and 40 months prior to clinical diagnosis of pancreatic cancer (1995, Berthélemy et al., Ann. Intern. Med., 123:188–191). Similarly, 24% of hyperplastic foci examined had a K-ras mutation (1996, Tada et al., Gastroent., 110:227–231).

5.4.2 Detection of CaSm Gene Products

Antibodies directed against wild type or mutant CaSm gene products or conserved variants or peptide fragments thereof, which are discussed, above, in Section 5.2, may also be used as diagnostics and prognostics, as described herein. Such diagnostic methods, may be used to detect abnormalities in the level of CaSm gene expression, or abnormalities in the structure and/or temporal, tissue, cellular, or subcellular location of CaSm gene product. Antibodies, or fragments of antibodies, such as those described below, may be used to screen potentially therapeutic compounds in vitro to determine their effects on CaSm gene expression and CaSm peptide production. The compounds which have beneficial effects on cancer can be identified and a therapeutically effective dose determined.

The tissue or cell type to be analyzed will generally include those which are known, or suspected, to express the CaSm gene, such as, for example, pancreatic cancer cells or metastatic cells. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cell taken from culture may be a necessary step to test the effect of compounds on the expression of the CaSm gene.

Preferred diagnostic methods for the detection of CaSm gene products or conserved variants or peptide fragments thereof, may involve, for example, immunoassays wherein the CaSm gene products or conserved variants, including gene products which are the result of alternatively spliced transcripts, or peptide fragments are detected by their interaction with an anti-CaSm gene product-specific antibody.

For example, antibodies, or fragments of antibodies, such as those described, above, in Section 5.3, useful in the present invention may be used to quantitatively or qualitatively detect the presence of CaSm gene products or conserved variants or peptide fragments thereof. The antibodies (or fragments thereof) useful in the present invention may, additionally, be employed histologically, as in immunofluorescence or immunoelectron microscopy, for in situ detection of CaSm gene products or conserved variants or peptide fragments thereof. In situ detection may be accomplished by removing a histological specimen from a patient, such as paraffin embedded sections of breast tissues and applying thereto a labeled antibody of the present invention. The antibody (or fragment) is preferably applied by overlaying the labeled antibody (or fragment) onto a biological sample. It may also be desirable to introduce the antibody inside the cell, for example, by making the cell membrane permeable. Through the use of such a procedure, it is possible to determine not only the presence of the CaSm gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for CaSm gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying CaSm gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled CaSm gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-CaSm gene product antibody may be determined according to well known methods. Those skilled in the art will be able to determine operative and optimal assay conditions for each determination by employing routine experimentation.

One of the ways in which the CaSm gene peptide-specific antibody can be detectably labeled is by linking the same to an enzyme and use in an enzyme immunoassay (EIA)

(Voller, A., "The Enzyme Linked Immunosorbent Assay (ELISA)", 1978, Diagnostic Horizons 2:1–7, Microbiological Associates Quarterly Publication, Walkersville, Md.); Voller et al., 1978, J. Clin. Pathol. 31:507–520; Butler 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect CaSm gene peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In various embodiments, the present invention provides the measurement of CaSm gene products, and the uses of such measurements in clinical applications.

The measurement of CaSm gene product of the invention can be valuable in detecting and/or staging cancer in a subject, in screening of cancer in a population, in differential diagnosis of the physiological condition of a subject, and in monitoring the effect of a therapeutic treatment on a subject.

The present invention also provides for the detecting, diagnosing, or staging of cancer, or the monitoring of treatment of cancer by measuring in addition to CaSm gene product at least one other marker, such as receptors or differentiation antigens. For example, serum markers selected from, for example but not limited to, carcinoembryonic antigen (CEA), CA19-9, CA195, DUPAN-2, SPAN-1 and CA50 can be measured in combination with CaSm gene product to detect, diagnose, stage, or monitor treatment of pancreatic cancer. In another embodiment, the prognostic indicator is the observed change in different marker levels relative to one another, rather than the absolute levels of the markers present at any one time. These measurements can also aid in predicting therapeutic outcome and in evaluating and monitoring the overall disease status of a subject.

In a specific embodiment of the invention, CaSm gene product alone or in combination with other markers can be measured in any body fluid of the subject including but not limited to blood, serum, plasma, milk, urine, saliva, pleural effusions, synovial fluid, spinal fluid, tissue infiltrations and tumor infiltrates. The measurement of CaSm gene products in blood or serum is preferred with respect to the development of a test kit which is to be used in clinics and homes.

Any of numerous immunoassays can be used in the practice of the instant invention, such as those described in Section 5.4.2. Antibodies, or antibody fragments containing the binding domain, which can be employed include but are not limited to suitable antibodies among those in Section 5.3 and other antibodies known in the art or which can be obtained by procedures standard in the art such as those described in Section 5.3.

5.4.3 Detecting and Staging a Cancer in a Subject

In one embodiment of the present invention, measurement of CaSm gene product or fragment thereof, or circulating CaSm gene product can be used to detect cancer in a subject or to stage the cancer in a subject.

Staging refers to the grouping of patients according to the extent of their disease. Staging is useful in choosing treatment for individual patients, estimating prognosis, and comparing the results of different treatment programs. Staging of cancer is performed initially on a clinical basis, according to the physical examination and laboratory radiologic evaluation.

Pancreatic cancer diseases or conditions which may be detected and/or staged in a subject according to the present invention include but are not limited to those listed in Table I (Beazley & Cohen, Ch. 15, page 255, in "Clinical Oncology", 2nd ed., ed. by Murphy et al., American Cancer Society, 1995).

TABLE I

STAGING OF PANCREATIC CANCER

PRIMARY TUMORS (T)

| | |
|---|---|
| TX | Primary tumor cannot be assessed |
| T0 | No evidence of primary tumor |
| T1 | Tumor limited to the pancreas |
| T1a | Tumor 2 cm or less in greatest dimension |
| T1b | Tumor more than 2 cm in greatest dimension |
| T2 | Tumor extends directly to any of the following: duodenum, bile duct or peripancreatic tissues |
| T3 | Tumor extends directly to any of the following: stomach, spleen, colon or adjacent large vessels |

REGIONAL LYMPH NODES (N)

| | |
|---|---|
| NX | Regional lymph nodes cannot be assessed |
| N0 | No regional lymph node metastasis |
| N1 | Regional lymph nodes metastasis |

DISTANT METASTASIS (M)

| | |
|---|---|
| MX | presence of distant metastasis cannot be assessed |
| M0 | No distant metastasis |
| M1 | Distant metastasis |

Stage Grouping

| | | | |
|---|---|---|---|
| Stage I | T1 | N0 | M0 |
| | T2 | N0 | M0 |
| Stage II | T3 | N0 | M0 |
| Stage III | Any T | N1 | M0 |
| Stage IV | Any T | Any N | M1 |

Any immunoassay, such as those described in Section 5.4.2 can be used to measure the amount of CaSm gene product which is compared to a baseline level. This baseline level can be the amount which is established to be normally present in the tissue or body fluid of subjects with various degrees of the disease or disorder. An amount present in the tissue or body fluid of the subject which is similar to a standard amount, established to be normally present in the tissue or body fluid of the subject during a specific stage of cancer, is indicative of the stage of the disease in the subject. The baseline level could also be the level present in the subject prior to the onset of disease or the amount present during remission of the disease.

In specific embodiments of this aspect of the invention, measurements of levels of the CaSm gene product can be used in the detection of pancreatic cancer or the presence of metastases or both.

In another embodiment of the invention, the measurement of CaSm gene product, fragments thereof or immunologically related molecules can be used to differentially diagnose in a subject a particular disease phenotype or physiological condition as distinct as from among two or more phenotypes or physiological conditions. To this end, for example, the measured amount of the CaSm gene product is compared with the amount of the molecule normally present in body fluid of a subject with one of the suspected physiological conditions. A measured amount of the molecule similar to the amount normally present in a subject with one of the physiological conditions, and not normally present in a subject with one or more of the other physiological conditions, is indicative of the physiological condition of the subject. Elevated levels of CaSm gene product in a subject relative to the baseline level can be indicative of the existence of cancer in the subject.

5.4.4 Monitoring the Effect of a Therapeutic Treatment

The present invention provides a method for monitoring the effect of a therapeutic treatment on a subject who has undergone the therapeutic treatment.

Clinicians very much need a procedure that can be used to monitor the efficacy of these treatments. CaSm gene product can be identified and detected in cancer patients with different manifestations of disease, providing a sensitive assay to monitor therapy. The therapeutic treatments which may be evaluated according to the present invention include but are not limited to radiotherapy, surgery, chemotherapy, vaccine administration, endocrine therapy, immunotherapy, and gene therapy, etc. The chemotherapeutic regimens include, but are not limited to administration of drugs such as, for example, fluorouracil and taxol.

The method of the invention comprises measuring at suitable time intervals before, during, or after therapy, the amount of a CaSm gene product. Any change or absence of change in the amount of the CaSm gene product can be identified and correlated with the effect of the treatment on the subject, such as, for example, a reduction of the transformed phenotype in cancer cells.

In a preferred aspect, the approach that can be taken is to determine the levels of CaSm gene product levels at different time points and to compare these values with a baseline level. The baseline level can be either the level of the marker present in normal, disease free individuals; and/or the levels present prior to treatment, or during remission of disease, or during periods of stability. These levels can then be correlated with the disease course or treatment outcome. Elevated levels of CaSm gene product relative to the baseline level indicate a poor response to treatment.

5.5 Screening Assays for Compounds that Modulate CaSm Activity

The present invention further provides methods for the identification of compounds that may, through its interaction with the CaSm gene or CaSm gene product, affect the onset, progression and metastatic spread of cancer; especially pancreatic cancer.

The following assays are designed to identify: (i) compounds that bind to CaSm gene products, including mammalian and non-mammalian homologs of CaSm; (ii) compounds that bind to other intracellular proteins that interact with a CaSm gene product, including mammalian and non-mammalian homologs of CaSm; (iii) compounds that interfere with the interaction of the CaSm gene product, including mammalian and non-mammalian homologs of CaSm, with other intracellular proteins; and (iv) compounds that modulate the activity of CaSm gene (i.e., modulate the level of CaSm gene expression and/or modulate the level of CaSm gene product activity).

Assays may additionally be utilized which identify compounds which bind to CaSm gene regulatory sequences (e.g., promoter sequences). See e.g., Platt, 1994, J. Biol. Chem. 269:28558–28562, which is incorporated herein by reference in its entirety, which may modulate the level of CaSm gene expression. Also provided is a method for identifying compounds that modulate CaSm gene expression, comprising: (a) contacting a test compound with a cell or cell lysate containing a reporter gene operatively associated with a CaSm gene regulatory element; and (b)detecting expression of the reporter gene product. Also provided is another method for identifying compounds that modulate CaSm gene expression comprising: (a) contacting a test compound with a cell or cell lysate containing CaSm transcripts; and (b) detecting the translation of the CaSm transcript. Any reporter gene known in the art can be used, such as but limited to, green fluorescent protein, β-galactosidease, alkaline phosphatase, chloramphenicol acetyltransferase, etc.

As described in sections 5.2 and 6.2.2, the CaSm gene product and homologs of CaSm, comprises two sequence motifs that are characteristics of a family of proteins which are components of the small nuclear ribonucleoprotein. These motifs, named Sm motif 1, and Sm motif 2 are required for interaction among members of the spliceosomal protein family. Although the CaSm gene product is not likely to be a member of this family of Sm proteins, the CaSm gene product may interact with intracellular proteins bearing one or both of these Sm motifs, including the Sm proteins. Furthermore, in view of the ability of the yeast CaSm homolog to act as a bypass suppressor in yeast cells carrying a mutant Pab1p gene, the CaSm gene product may also interact with proteins associated with the poly(A) tail and the 5' cap structure of eukaryotic mRNA, including Pab1p, translation initiation complex, and the like.

Such intracellular proteins may be involved in uncontrolled cell growth and in the onset, development and metastatic spread of cancer.

Compounds identified via assays such as those described herein may be useful, for example, in elaborating the biological functions of the CaSm gene product, and for ameliorating symptoms of cancer. Assays for testing the effectiveness of compounds, identified by, for example, techniques such as those described in Section 5.5.1, are discussed, below, in Section 5.5.3. Fragments of CaSm protein useful in these assays, may include but not limited to, peptides corresponding to the CaSm Sm motif 1 and CaSm Sm motif 2 or portions thereof; and truncated CaSm in which the Sm motif 1 or Sm motif 2 or both motifs are deleted. It is to be noted that the compositions of the invention include pharmaceutical compositions comprising one or more of the compounds identified via such methods. Such pharmaceutical compositions can be formulated, for example, as discussed, below, in Section 5.7.

5.5.1 In vitro Screening Assays for Compounds that Bind to the CaSa Gene Product In vitro systems may be designed to identify compounds capable of interacting with, e.g., binding to, the CaSm gene products of the invention and homologs of CaSm (e.g., the yeast homolog encoded by ORF YJL124c). Compounds identified may be useful, for example, in modulating the activity of wild type and/or mutant CaSm gene products, may be useful in elaborating the biological function of the CaSm gene product, may be utilized in screens for identifying compounds that disrupt normal CaSm gene product interactions, or may in themselves disrupt such interactions. Such interactions can be mediated by the Sm motif 1, Sm motif 2 or both.

The principle of the assays used to identify compounds that interact with the CaSm gene product involves preparing a reaction mixture of the CaSm gene product, or fragments thereof and the test compound under conditions and for a time sufficient to allow the two components to interact with, e.g., bind to, thus forming a complex, which can represent a transient complex, which-can be removed and/or detected in the reaction mixture. These assays can be conducted in a variety of ways. For example, one method to conduct such an assay would involve anchoring CaSm gene product or the test substance onto a solid phase and detecting CaSm gene product/test compound complexes anchored on the solid phase at the end of the reaction. In one embodiment of such a method, the CaSm gene product or fragment thereof may be anchored onto a solid surface, and the test compound, which is not anchored, may be labeled, either directly or indirectly.

In practice, microtitre plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for CaSm gene product or the test compound to anchor any complexes formed in solution, and a labeled antibody specific for the other component of the possible complex to detect anchored complexes.

5.5.2 Assays for Intracellular Proteins that Interact with the CaSm Gene Product Any method suitable for detecting protein-protein interactions may be employed for identifying CaSm protein-intracellular protein interactions, especially interactions mediated by the Sm motif 1, or Sm motif 2 or both.

Among the traditional methods which may be employed are co-immunoprecipitation, crosslinking and co-purification through gradients or chromatographic columns. Utilizing procedures such as these allows for the isolation of intracellular proteins which interact with CaSm gene products, fragments of CaSm gene product, and homologs of CaSm (e.g., the yeast homolog encoded by ORF YJL124c). Once isolated, such an intracellular protein can be identified and can, in turn, be used, in conjunction with standard techniques, to identify additional proteins with which it interacts. For example, at least a portion of the amino acid sequence of the intracellular protein which interacts with the CaSm gene product can be ascertained using techniques well known to those of skill in the art, such as via the Edman degradation technique (see, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of genes which encode the intracellular protein interacting with the CaSm protein. These methods include, for example, probing expression libraries with labeled CaSm protein or fragments thereof (e.g., Sm motif 1, Sm motif 2), using CaSm protein of fragments thereof in a manner similar to the well known technique of antibody probing of λgt11 libraries.

One method which detects protein interactions in vivo, the two-hybrid system, can be used. One version of this system has been described (Chien et al., 1991, Proc. Natl. Acad. Sci. USA, 88:9578–9582) and is commercially available from Clontech (Palo Alto, Calif.).

5.5.3 Assays for Compounds that Interfere with CaSm Gene Product/intracellular Macromolecular Interaction The CaSm gene products of the invention, fragments thereof, and homologs of CaSm (e.g., the yeast homolog encoded by ORF YJL124c) may, in vivo, interact with one or more intracellular macromolecules, such as proteins and nucleic acid molecules. Such macromolecules may include, but are not limited to, RNA (including polyadenylated (poly(A)) RNA and RNA with the 5' cap structure) and those proteins identified via methods such as those described, above, in Section 5.5.2. For purposes of this discussion, such intracellular macromolecules are referred to herein as "interacting partners". Compounds that disrupt CaSm interactions in this way may be useful in regulating the activity of the CaSm gene product, including mutant CaSm gene products. Such compounds may include, but are not limited to molecules such as peptides, and the like, as described, for example, in Section 5.5.1. above, which would be capable of gaining access to the intracellular CaSm gene product. Such compounds may also include peptides or modified peptides comprising the amino acid sequence of Sm motif 1, Sm motif 2 or both.

The basic principle of the assay systems used to identify compounds that interfere with the interaction between the CaSm gene product and its intracellular interacting partner or partners involves preparing a reaction mixture containing the CaSm gene product, or fragments thereof, and the interacting partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of CaSm gene product and its intracellular interacting partner. Control reaction mixtures are incubated without the test compound or with a placebo. The formation of any complexes between the CaSm gene product or fragments thereof and the intracellular interacting partner is then detected. The formation of a complex in the control reaction, but not in the reaction mixture containing the test compound, indicates that the compound interferes with the interaction of the CaSm gene protein and the interacting partner. Additionally, complex formation within reaction mixtures containing the test compound and normal CaSm gene protein may also be compared to complex formation within reaction mixtures containing the test compound and a mutant CaSm gene protein. This comparison may be important in those cases wherein it is desirable to identify compounds that disrupt interactions of mutant but not normal CaSm gene proteins.

The assay for compounds that interfere with the interaction of the CaSm gene product and interacting partners can be conducted in a heterogeneous or homogeneous format. Heterogeneous assays involve anchoring either the CaSm gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the CaSm gene products and the interacting partners, e.g., by competition, can be identified by conducting the reaction in the presence of the test substance; i.e., by adding the test substance to the reaction mixture prior to or simultaneously with the CaSm gene protein and intracellular interacting partner. Alternatively, test compounds that disrupt pre-formed complexes, e.g. compounds with higher binding constants that displace one of the components from the complex, can be tested by adding the test compound to the reaction mixture after complexes have been formed. The various formats are described briefly below.

In a heterogeneous assay system, either the CaSm gene product or the interacting partner, is anchored onto a solid surface, while the non-anchored species is labeled, either directly or indirectly. In practice, microtitre plates are conveniently utilized. The anchored species may be immobilized by non-covalent or covalent attachments. Non-covalent attachment may be accomplished simply by coating the solid surface with a solution of the CaSm gene product or interacting partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt pre-formed complexes can be detected.

Alternatively, the reaction can be conducted in a liquid phase in the presence or absence of the test compound, the reaction products separated from unreacted components, and complexes detected; e.g., using an immobilized antibody specific for one of the interacting components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the CaSm gene protein and the interacting partner is prepared in which either the CaSm gene product or its interacting partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt CaSm gene protein/intracellular interacting partner interaction can be identified.

In a particular embodiment, the CaSm gene product or fragments thereof can be prepared for immobilization using recombinant DNA techniques described in Section 5.1, above. For example, the CaSm coding region can be fused to a glutathione-S-transferase (GST) gene using a fusion vector, such as pGEX-5X-1, in such a manner that its interacting activity is maintained in the resulting fusion protein. The intracellular interacting partner can be purified and used to raise a monoclonal antibody, using methods routinely practiced in the art and described above, in Section 5.2. This antibody can be labeled with the radioactive isotope $^{125}$I, for example, by methods routinely practiced in the art. In a heterogeneous assay, e.g., the GST-CaSm fusion protein can be anchored to glutathione-agarose beads. The intracellular interacting partner can then be added in the presence or absence of the test compound in a manner that allows interaction, e.g., binding, to occur. At the end of the reaction period, unbound material can be washed away, and the labeled monoclonal antibody can be added to the system and allowed to bind to the complexed components. The interaction between the CaSm gene protein and the intracellular interacting partner can be detected by measuring the amount of radioactivity that remains associated with the glutathione-agarose beads. A successful inhibition of the interaction by the test compound will result in a decrease in measured radioactivity.

Alternatively, the GST-CaSm gene fusion protein and the intracellular interacting partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the CaSm gene product/interacting partner interaction can be detected by adding the labeled antibody and measuring the radioactivity associated with the beads.

5.5.4 Cell-based Assays for Identification of Compounds which Modulate CaSm Activity Cell-based methods are presented herein which identify compounds capable of treating cancer by modulating CaSm activity. Specifically, such assays identify compounds which affect CaSm-dependent processes, such as but not limited to cell viability, changes in cell morphology, cell division, differentiation, adhesion, motility, or phosphorylation, dephosphorylation of cellular proteins. Other CaSm-dependent processes which may be affected include but are not limited to stimulation of translation, binding of ribosome to mRNA, protection of mRNA from decapping or degradation. Compounds identified via such methods can, for example, be utilized in methods for treating cancer and metastasis.

In one embodiment, the cell-based assay uses recombinant yeast cells that comprise an expression construct producing the CaSm gene product or the yeast homolog of CaSm, and have mutations in the genes encoding respectively, the poly(A) binding protein, Pab1p, and the large subunit of the translation initiation complex, eIF-4G. Mutant yeast cells that have non-functional mutations in the genes encoding Pab1p and eIF-4G are not viable except in the presence of CaSm or the CaSm homolog which serves as a bypass suppressor. In this assay, mutant yeast cells producing CaSm or a CaSm homolog are exposed to a test compound for an interval sufficient for the compound to modulate the activity of the CaSm or CaSm homolog. The activity of CaSm in the presence of the test compound is assessed by the viability or growth of the mutant yeast cells. For example, a compound that inhibits the activity of CaSm would grow poorly or would not be viable. It is contemplated that similar assays can be carried out using mammalian CaSm in mammalian cells that have mutations in genes encoding the functional equivalents of the poly(A) binding protein, Pab1p and the large subunit of translation initiation complex, eIF4G, which are highly conserved.

In another embodiment, the cell-based assays are based on expression of the CaSm gene product in a mammalian cell and measuring the CaSm-dependent process. Any mammalian cells that can express the CaSm gene and allow the functioning of the CaSm gene product can be used, in particular, cancer cells derived from the pancreas, such as CAPAN-1, CAPAN-2, ASPC-1, PANC-1 and HPAC. Other cancer cell lines such as those derived from prostate, liver, ovary, lung, rectum, kidney and non-erythroid hemopoietic cells, may also be used provided that a detectable CaSm gene product is produced. Recombinant expression of the CaSm gene in these cells or other normal cells can be achieved by methods described in Section 5.2. In these assays, cells producing functional CaSm gene products are exposed to a test compound for an interval sufficient for the compound to modulate the activity of the CaSm gene product. The activity of CaSm gene product can be measured directly or indirectly through the detection or measurement of CaSm-dependent cellular processes such as, for example, the manifestation of a transformed phenotype. As a control, a cell not producing the CaSm gene product may be used for comparisons. Depending on the cellular process, any techniques known in the art may be applied to detect or measure it.

5.6 Methods for Treatment of Cancer

Described below are methods and compositions for treating cancer using the CaSm gene or gene product as a therapeutic target. The outcome of a treatment is to at least produce in a treated subject a healthful benefit, which in the case of cancer, includes but is not limited to remission of the cancer, palliation of the symptoms of the cancer, control of metastatic spread of the cancer.

All such methods involve modulating CaSm gene activity and/or expression which in turn modulate the phenotype of the treated cell.

As discussed, above, successful treatment of cancer can be brought about by techniques which serve to decrease CaSm activity. Activity can be decreased by, for example, directly decreasing CaSm gene product activity and/or by decreasing the level of CaSm gene expression.

For example, compounds such as those identified through assays described, above, in Section 5.5, which decrease CaSm activity can be used in accordance with the invention to treat cancer. As discussed in Section 5.5, above, such molecules can include, but are not limited to peptides, including soluble peptides, and small organic or inorganic molecules, and can be referred to as CaSm antagonists. Peptides comprising the amino acid sequence of Sm motif 1, Sm motif 2 or both, or portions thereof, that interfere with the interaction of CaSm with intracellular macromolecules may also be used. Techniques for the determination of effective doses and administration of such compounds are described, below, in Section 5.7.

Further, antisense and ribozyme molecules which inhibit CaSm gene expression can also be used in accordance with the invention to reduce the level of CaSm gene expression, thus effectively reducing the level of CaSm gene product present, thereby decreasing the level of CaSm activity. Still further, triple helix molecules can be utilized in reducing the level of CaSm gene activity. Such molecules can be designed to reduce or inhibit either wild type, or if appropriate, mutant target gene activity. Techniques for the production and use of such molecules are well known to those of skill in the art.

Any technique which serves to selectively administer nucleic acid molecules to a cell population of interest can be used, for example, by using a delivery complex. Such a delivery complex can comprise an appropriate nucleic acid molecule and a targeting means. Such targeting means can comprise, for example, sterols, lipids, viruses or target cell specific binding agents. Viral vectors that can be used with recombinant viruses include, but are not limited to adenovirus, adeno-associated virus, herpes simplex virus, vaccinia virus, and retrovirus vectors, in addition to other particles that introduce DNA into cells, such as liposomes.

5.6.1 Antisense Molecules

The use of antisense molecules as inhibitors of gene expression is a specific, genetically based therapeutic approach (for a review, see Stein, in Ch. 69, Section 5 "Cancer: Principle and Practice of Oncology", 4th ed., ed. by DeVita et al., J. B. Lippincott, Philadelphia 1993). The present invention provides the therapeutic or prophylactic use of nucleic acids of at least six nucleotides that are antisense to a gene or cDNA encoding CaSm or a portion thereof. An "antisense" CaSm nucleic acid as used herein refers to a nucleic acid capable of hybridizing to a portion of a CaSm RNA (preferably mRNA) by virtue of some sequence complementarity. The invention further provides pharmaceutical compositions comprising an effective amount of the CaSm antisense nucleic acids of the invention in a pharmaceutically acceptable carrier, as described infra.

In another embodiment, the invention is directed to methods for inhibiting the expression of a CaSm nucleic acid sequence in a mammalian cell in vitro or in vivo comprising providing the cell with an effective amount of a composition comprising an CaSm antisense nucleic acid of the invention.

The antisense nucleic acid of the invention may be complementary to a coding and/or noncoding region of a CaSm mRNA. The antisense molecules will bind to the complementary CaSm gene mRNA transcripts and reduce or prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Nucleic acid molecules that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, nucleic acid molecules complementary to either the 5'- or 3'- non-translated, non-coding regions of the CaSm gene, as shown, for example, in FIG. 6, could be used in an antisense approach to inhibit translation of endogenous CaSm gene mRNA.

Nucleic acid molecules complementary to the 5' untranslated region of the mRNA should include the complement of the AUG start codon. Antisense nucleic acid molecules complementary to mRNA coding regions are less efficient inhibitors of translation but could be used in accordance with the invention. Whether designed to hybridize to the 5'- 3'- or coding region of target or pathway gene mRNA, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, at least 50 nucleotides, or at least 200 nucleotides.

Regardless of the choice of target sequence, it is preferred that in vitro studies are first performed to quantitate the ability of the antisense molecule to inhibit gene expression, for example, as described below in Section 7.1. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The antisense molecule can be DNA or RNA or chimeric mixtures or derivatives or modified versions thereof, single-stranded or double-stranded. The antisense molecule can be modified at the base moiety, sugar moiety, or phosphate backbone, for example, to improve stability of the molecule, hybridization, etc. The antisense molecule may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the antisense molecule may be conjugated to another molecule, e.g., a peptide, hybridization triggered cross-linking agent, transport agent, hybridization-triggered cleavage agent, etc.

The antisense molecule may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense molecule may also comprise at least one modified sugar moiety selected from the group including but not limited to arabinose, 2-fluoroarabinose, xylulose, and hexose.

In yet another embodiment, the antisense molecule comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense molecule is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Antisense molecules of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the CaSm coding region, such as the ones described in Section 7.1, could be used, those complementary to the transcribed untranslated region are also preferred. For example, antisense oligonucleotides having the following sequence can be utilized in accordance with the invention:

a) 5'-CATTTTGAACTGAAATA-3' (SEQ ID NO:9) which is complementary to nucleotides −14 to +3 in FIG. 6.
b) 5'-CATTTTGAACTGAAATAATGCTGC-3' (SEQ ID NO:10) which is complementary to nucleotides −21 to +3 in FIG. 6.
c) 5'-CATTTTGAACTGAAATAATGCTGCAATGCAC-3' (SEQ ID NO:11) which is complementary to nucleotides −28 to +3 in FIG. 6.
d) 5'-CATTTTGAACTGAAATAATGCTGCAATGCACA GCGGCG-3' (SEQ ID NO:12) which is complementary to nucleotides −35 to +3 in FIG. 6.
e) 5'-GTTCATTTTGAACTGAAATAATGCTGCAATG CAC-3' (SEQ ID NO:13) which is complementary to nucleotides −28 to +6 in FIG. 6.
f) 5'-TTTGAACTGAAATAATGCTGCAATGCACAGCG GCG-3' (SEQ ID NO:14) which is complementary to nucleotides −35 to −1 in FIG. 6.
g) 5'-TAATGCTGCAATGCAC-3' (SEQ ID NO:15) which is complementary to nucleotides −28 to −13 in FIG. 6.

The CaSm antisense nucleic acids can be used to treat or prevent formation of cancer involving a cell type that expresses, or preferably overexpresses, CaSm. Cell types which express or overexpress CaSm RNA can be identified by various methods known in the art. Such methods include but are not limited to hybridization with a CaSm-specific nucleic acid (e.g., by Northern hybridization, dot blot hybridization, in situ hybridization); detection of CaSm gene product by immunoassays, etc. In a preferred aspect, primary tissue from a patient can be assayed for CaSm expression prior to treatment, e.g., by immunocytochemistry or in situ hybridization.

Pharmaceutical compositions of the invention comprising an effective amount of a CaSm antisense nucleic acid in a pharmaceutically acceptable carrier, can be administered to a patient having a disease or disorder which is of a type that expresses or overexpresses CaSm RNA or protein.

The amount of CaSm antisense nucleic acid which will be effective in the treatment of a particular disorder or condition will depend on the nature of the cancer or condition, and can be determined by standard clinical techniques. Where possible, it is desirable to determine the antisense cytotoxicity of the tumor type to be treated in vitro, and then in useful animal model systems prior to testing and use in humans.

The antisense molecules should be delivered to cells which express the CaSm gene in vivo. A number of methods have been developed for delivering antisense DNA or RNA to cells; e.g., antisense molecules can be injected directly into the tissue site, or modified antisense molecules, designed to target the desired cells (e.g., antisense molecule linked to peptides or antibodies that specifically bind receptors or antigens expressed on the target cell surface) can be administered systemically. Antisense molecules can be delivered to the desired cell population via a delivery complex. In a specific embodiment, pharmaceutical compositions comprising CaSm antisense nucleic acids are administered via biopolymers (e.g. poly-β-1->4-N-acetylglucosamine polysaccharide), liposomes, microparticles, or microcapsules. In various embodiments of the invention, it may be useful to use such compositions to achieve sustained release of the CaSm antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

However, it is often difficult to achieve intracellular concentrations of the antisense sufficient to suppress translation of endogenous mRNAs. Therefore a preferred approach utilizes a recombinant DNA construct in which the antisense oligonucleotide or polynucleotide is placed under the control of a strong pol III or pol II promoter. The use of such a construct to transfect target cells in the patient will result in the transcription of sufficient amounts of single stranded RNAs that will form complementary base pairs with the endogenous CaSm gene transcripts and thereby prevent translation of the CaSm gene mRNA. For example, as described in Section 7.1, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced either directly into the tissue site, or via a delivery complex. Alternatively, viral vectors can be used which selectively infect the desired tissue. Any of the methods for gene therapy available in the art, such as those described in Section 5.6.4 can be used. Exemplary methods are described below.

5.6.2 Ribozyme Molecules

Ribozymes are enzymatic RNA molecules capable of catalyzing the specific cleavage of RNA (For a review see, for example Rossi, J., 1994, Current Biology 4:469–471). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target gene proteins.

Ribozyme molecules designed to catalytically cleave CaSm gene mRNA transcripts can also be used to prevent translation of CaSm gene mRNA and expression of target or pathway gene. (See, e.g., PCT International Publication WO90/11364, published Oct. 4, 1990; Sarver et al., 1990, Science 247:1222–1225). While ribozymes that cleave mRNA at site specific recognition sequences can be used to destroy CaSm gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the CaSm gene mRNA; i.e., to increase efficiency and minimize the intracellular accumulation of non-functional mRNA transcripts.

For example, hammerhead ribozymes having the following sequences can be utilized in accordance with the invention:

a) 5'-GTTCAAAGCNGNNNNNNCNGAGNAGUCTTG AAC-3' (SEQ ID NO:16) which will cleave human CaSm mRNA between nucleotides −1 and +1 in FIG. 6.
b) 5'-AGGCAAAGCNGNNNNNNCNGAGNAGUCATA GTT-3' (SEQ ID NO:17) which will cleave human CaSm mRNA between nucleotides +9 and +10 in FIG. 6.
c) 5'-CTGCAAAGCNGNNNNNNCNGAGNAGUCTGC ACA-3' (SEQ ID NO:18) which will cleave human CaSm mRNA between nucleotides −23 and −24 in FIG. 6.
d) 5'-CGCCAAAGCNGNNNNNNCNGAGNAGUCCGC GTC-3' (SEQ ID NO:19) which will cleave human CaSm mRNA between nucleotides −44 and −45 in FIG. 6.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in an CaSm gene.

As in the antisense approach, the ribozymes can be composed of modified oligonucleotides (e.g. for improved stability, targeting, etc.) and should be delivered to cells which express the CaSm gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous CaSm gene messages and inhibit translation. Because ribozymes unlike antisense molecules, are catalytic, a lower intracellular concentration is required for efficiency.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. These nucleic acid constructs can be administered selectively to the desored cell population via a delivery complex.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.6.3 Therapeutic Antibodies

Antibodies exhibiting capability to downregulate CaSm gene product activity can be utilized to treat cancer. Such antibodies can be generated using standard techniques described in Section 5.3, above, against full length wild type or mutant CaSm proteins, or against peptides corresponding to portions of the proteins such as, for example, the Sm motif 1 or Sm motif 2. The antibodies include but are not limited to polyclonal, monoclonal, Fab fragments, single chain antibodies, chimeric antibodies, and the like.

Because CaSm is an intracellular protein, it is preferred that internalizing antibodies be used. However, lipofectin or liposomes can be used to deliver the antibody or a fragment of the Fab region which binds to the CaSm gene product epitope into cells. Where fragments of the antibody are used, the smallest inhibitory fragment which binds to the CaSm protein's binding domain is preferred. For example, peptides having an amino acid sequence corresponding to the domain of the variable region of the antibody that binds to the CaSm protein can be used. Such peptides can be synthesized chemically or produced via recombinant DNA technology using methods well known in the art (e.g., see Creighton, 1983, supra; and Sambrook et al., 1989, above). Alternatively, single chain antibodies, such as neutralizing antibodies, which bind to intracellular epitopes can also be administered. Such single chain antibodies can be administered, for example, by expressing nucleotide sequences encoding single-chain antibodies within the target cell population by utilizing, for example, techniques such as those described in Marasco et al. (1993, Proc. Natl. Acad. Sci. USA 90:7889–7893).

5.6.4 Gene Therapy

Gene therapy refers to treatment or prevention of cancer performed by the administration of a nucleic acid to a subject who has cancer or in whom prevention or inhibition of cancer is desirable. In this embodiment of the invention, the therapeutic nucleic acid produces intracellularly an antisense nucleic acid molecules that mediates a therapeutic effect by inhibiting CaSm expression. In another embodiment, nucleic acids comprising a sequence encoding a dominant negative mutant CaSm protein or non-functional fragment or derivative thereof, are administered to inhibit CaSm function by interfereing with the interactions of CaSm and with other molecules in the cell.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5) :155–215). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds.), 1994, Current Protocols in Human Genetics, John Wiley & Sons, NY.

In one aspect, the therapeutic nucleic acid comprises a CaSm nucleic acid that is part of an expression vector that expresses a dominant non-functional CaSm protein or fragment or chimeric protein thereof in cancer cells. The function of CaSm is thought to be mediated by protein-protein interactions. Therefore, CaSm mutants that are defective in function but effective in binding to its interacting partner can be used as a dominant negative mutant to compete with the wild type CaSm. Dominant non-functional CaSm can be engineered for expression in cancer cells that inappropriately overexpress CaSm.

In a preferred aspect, the therapeutic nucleic acid comprises an antisense CaSm nucleic acid that is part of an expression vector that produces the antisense molecule in a suitable host. In particular, such a nucleic acid has a promoter operably linked to the antisense CaSm sequence, said promoter being inducible or constitutive, and, optionally, tissue-specific.

In another particular embodiment, a nucleic acid molecule is used in which the antisense CaSm sequences and any other desired sequences are flanked by regions that promote homologous recombination at a desired site in the genome, thus providing for intrachromosomal expression of the antisense CaSm nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector or a delivery complex, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the antisense nucleic acid molecule or encoded non-functional CaSm gene product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in biopolymers (e.g., poly-β-1->4-N-acetylglucosamine polysaccharide; see U.S. Pat. No. 5,635, 493), encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the antisense CaSm nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The antisense CaSm nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdrl gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234.

Adeno-associated virus (AAV) has also been proposed for use in gene therapy (Walsh et al., 1993, Proc. Soc. Exp. Biol. Med. 204:289–300).

The form and amount of therapeutic nucleic acid envisioned for use depends on the cancer, desired effect, patient state, etc., and can be determined by one skilled in the art.

A less preferred approach to gene therapy involves transferring an antisense CaSm gene or a dominant non-functional CaSm gene to cancer cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient, for purpose of replacing cells that are overexpressing CaSm. In this embodiment, the nucleic acid is introduced into a cancer cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92). The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment,recombinant blood cells (e.g., hematopoietic stem or progenitor cells) are preferably administered intravenously.

Endogenous CaSm gene expression can also be reduced by inactivating or "knocking out" the gene or its promoter using targeted homologous recombination, (e.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional CaSm gene (or a completely unrelated DNA sequence) flanked by DNA homologous to the endogenous CaSm gene (either the coding regions or regulatory regions of the CaSm gene) can be used, with or without a selectable marker and/or a negative selectable marker, to transfect cells that express CaSm gene in vivo. Insertion of the DNA construct, via targeted homologous recombination, results in inactivation of the CaSm gene. Such approaches are particularly suited where modifications to ES (embryonic stem) cells can be used to generate animal offspring with an inactive CaSm gene (e.g., see Thomas & Capecchi 1987 and Thompson 1989, supra). Such techniques can also be utilized to generate animal models of cancer. It should be noted that this approach can be adapted for use in humans provided the recombinant DNA constructs are directly administered or targeted to the required site in vivo using appropriate viral vectors, e.g., herpes virus vectors.

Alternatively, endogenous CaSm gene expression can be reduced by targeting deoxyribonucleotide sequences complementary to the regulatory region of the CaSm gene (i.e., the CaSm gene promoter and/or enhancers) to form triple helical structures that prevent transcription of the CaSm gene in target cells in the body. (See generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15).

5.7 Pharmaceutical Preparations and Methods of Administration

The compounds and nucleic acid sequences described herein can be administered to a patient at therapeutically effective doses to treat or prevent cancer. A therapeutically effective dose refers to that amount of a compound sufficient to result in a healthful benefit in the treated subject. Formulations and methods of administration that can be employed when the therapeutic composition comprises a nucleic acid are described in Section 5.6.4.

5.7.1 Effective Dose

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

5.7.2 Formulations and Use

Pharmaceutical compositions for use in accordance with the present invention can be formulated in conventional manner using one or more physiologically acceptable carriers or excipients.

Thus, the compounds and their physiologically acceptable salts and solvents can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

6. EXAMPLE

Identification of a Novel Gene Involved in Cancer

This example describes the isolation and characterization of the CaSm gene. Subtractive hybridization cloning was undertaken in order to isolate genes whose expression is associated with pancreatic cancer. The CaSm gene which is overexpressed in pancreatic cancer cells was selected for detailed characterization.

6.1. Materials and Methods

Cell Lines

The cell lines HS680.PAN, CAPAN-1 and PANC-1 were obtained from American Type Culture Collection (Rockville, Md.). They were maintained in DMEM/10% FBS, RPMI 1640/15% FBS and DMEM/10% FBS, respectively. Transfection of PANC-1 cells was performed in 35 mm wells using 2 µg of DNA and 10 µl of LipofectAmine (Fibco-BRL, Bethesda, Md.) per well (60–80% confluent). Stable transfectants were selected in 500 µg/ml G418. Soft agar growth assays were performed in 6-well plates (35 mm wells). Duplicate assays initiated with 1000, 5000, and 25,000 cells were scored after three weeks. The soft agar assay was performed twice, independently.

Tissue and Serum Samples

Human tissues were procured from The Cooperative Human Tissue Network, Mt. Sinai Medical Center in Miami Beach, Fla. (from Dr. Saul Suster) and from The Medical University of South Carolina.

RNA Isolation and Analysis

RNA from cultured cells and from human tissues was purified using RNAzol B (Tel-Test, Inc., Friendswood, Tex.) according to the manufacturer's protocol. Total RNA was fractionated on 1.2 or 1.5% agarose gels containing 0.66 M formaldehyde (2.2 M in the sample) by the method of Lehrach et al. (1977, Biochem., 16:4743–4751). RNA separated in gels were transferred to Duralon filters (Stratagene) in 0.1 M sodium phosphate, pH 6.8, UV crosslinked, and hybridized to labelled nucleic acid molecules in Quik-Hyb (Stratagene) according to the manufacturer's instructions.

RNA quantity and quality were monitored by ethidium bromide visualization of the 28S and 18S ribosomal bands.

6.2. Results

6.2.1. Cloning of Cancer-Associated Genes

Differentially expressed mRNAs in pancreatic cancer were first identified by performing subtractive hybridization between the pancreatic cancer cell line CAPAN-1 and the diploid, more normal pancreatic epithelial cell line HS680.PAN. Subtractive hybridization was performed as described previously (1990, Schweinfest et al., Genet. Anal. Tech. Appl., 7:64–70; 1993, Schweinfest et al., Proc. Natl. Acad. Sci., USA, 90:4166–4170). Complementary DNA (cDNA) clones obtained by subtractive hybridization were confirmed to be differentially expressed by two methods.

First, DNA from 600 subtractive cDNA clones was dot blotted onto nylon membranes and analyzed by hybridization with labelled total cDNA from CAPAN-1 and HS680.PAN mRNA. Clone CA3–30 exhibiting differential hybridization was isolated from among the subtractive library clones. The full-length sequence partially contained in CA3-30 is referred to as the CaSm gene. The original CA3-30 cDNA clone was used to isolate a full length clone of the CaSm gene by standard technique. CaSm was among those clones that had a much stronger hybridization signal with CAPAN-1 cDNA compared to HS680.PAN cDNA.

Second, CaSm cDNA insert (along with other tentatively identified differentially expressed cDNA clones) was labeled and used to probe a northern blot of tumor and normal pancreatic tissue RNAs. FIG. 1 shows a representative northern blot for CaSm that includes both matched pairs of samples (tumor and normal tissues from the same patient) as well as individual tumor and normal specimens. Eight of nine matched pairs show significantly higher levels of a 1.2 kb CaSm mRNA in tumor/pancreatitis compared to normal. The absolute level of CaSm mRNA is somewhat variable among the samples such that some tumor samples express less mRNA than non-matched normal samples (e.g., compare lane 17T to lane 18N). However, the matched samples show a consistent pattern of overexpression in tumor tissue. Nine of nine individual tumor/pancreatitis specimens show high levels of CaSm mRNA, comparable to the levels in the matched tumor specimens.

In addition to pancreatic cancer, CaSm mRNA is expressed in normal thymus, breast, colon, spleen and esophagus tissues; low levels of expression are seen in normal pancreas, lung, brain, placenta, kidney, ovary, testis, and heart (FIG. 2A). Several pancreatic cancer cell lines express high levels of CaSm mRNA. These include CAPAN-1, CAPAN-2, AsPC-1, PANC-1, and HPAC (FIG. 2B). Other cancer-derived cell lines that express high levels of CaSm mRNA include those from prostate (PC-3), liver (SK-HEP-1), ovary (OVCAR-3), lung (A-427), rectum (SW1463), kidney (Caki-1) and nonerythroid hematopoietic cells (MOLT-4, NC-37, Raji, H9, KG-1) (FIG. 2B), and mesothelioma. The results show that the expression of the CaSm gene is up-regulated in cancer cells, especially pancreatic cancer cells. The results also show that the cancer cell lines from liver (SK-HEP-1), ovary (OVCAR-3), lung (A427) and kidney (Caki-1) show increased CaSm expression compared to their normal tissue cognates (compare FIGS. 2A and 2B).

Moreover, a variant of CaSm which has a lower molecular weight has been identified by polymerase chain reaction. This variant apparently lacks amino acids 22–32 of Sm motif 1 and all of Sm motif 2.

6.2.2. The CaSm cDNA

A full length clone comprising the CaSm cDNA was isolated and sequenced, and was found to consist of 894 nucleotides including a polyadenylation signal at nucleotides 878–883. The translational start signal is contained within the sequence TCAAAATGA (nucleotides 160–168), which contains the requisite purines at positions −3 and +4 (1991, Kozak et al., J. Cell Biol., 115:887–903). The largest open reading frame can encode a 133 amino acid polypeptide (nucleotides 165–563) of predicted molecular weight 15,179 daltons and isoelectric point of 4.97. The predicted open reading frame (ORF) of CaSm was confirmed by its expression in a coupled transcription and translation reaction. The putative coding strand translates an 18 kilodalton polypeptide, which is somewhat larger than the 15.2 kd molecular weight predicted from its deduced amino acid sequence. The putative non-coding strand produces a much smaller product. Furthermore, only antisense probe to the putative coding strand hybridizes to mRNA from pancreatic cancer cells, thus, confirming the expression of the predicted ORF.

No significant similarities were found to any motifs listed in the PROSITE database. However, the 133 amino acid polypeptide of CaSm shares significant homology with the snRNP Sm G protein (FIG. 3A). A computerized BESTFIT of CaSm and human Sm G protein is 32% identical and 60% similar (allowing for conservative amino acid substitutions). This similarity is nearly completely confined to the amino terminal half of CaSm (amino acids 4–78). Interestingly, this homology localizes to the two Sm motifs that characterize the Sm protein family (Hermann et al., 1995, EMBO J., 14:2076–2088). Sm motif 1 and Sm motif 2, 32 and 14 amino acids respectively, are responsible for protein-protein interactions, presumably necessary for the assembly of snRNP complexes (Hermann et al., 1995, EMBO J., 14:2076–2088). The level of identity between CaSm and Sm G protein is low (32%) compared to the level of identity between the Sm G proteins of very distantly related species such as plants and yeast (>50% identity). Other Sm proteins from snRNPs are even less similar to CaSm than Sm G. Moreover, at 133 amino acids, the CaSm gene product is nearly twice the size of human Sm G protein (76 amino acids). Finally, with the exception of Sm F protein (pI=4.6), all the Sm proteins have basic isoelectric points (Woppmann et al., 1990, Nuc. Acids Res., 18:4427–4438). Therefore, it seems unlikely that CaSm is a true member of the Sm protein family. Nonetheless, most key features that constitute the Sm motifs are retained in CaSm. Specifically, the 100% conserved glycine and asparagine residues at positions 13 and 23, respectively, of Sm motif 1 are also found in CaSm. Overall, 12 of the 15 defined positions in the consensus for Sm motif 1 are conserved in CaSm. Furthermore, 10 of the 11 defined positions in the Sm motif 2 consensus are also conserved in CaSm (see FIG. 3A).

Among known proteins, the predicted CaSm protein is most similar to the human Sm G protein, a "common protein" component of the snRNP (1995, Hermann et al., EMBO J., 14:2076–2088). Interestingly, the region of greatest homology is in the so-called Sm motifs 1 and 2 that characterize the Sm proteins. These motifs are required for protein-protein interaction among members of the Sm protein family, however they are also found in proteins that do not belong to the major Sm protein family (1995, Hermann et al., EMBO J., 14:2076–2088). All 8 snRNP common core proteins have been cloned and sequenced, yet CaSm shares only limited homology with this group. Therefore, CaSm is not likely to be a member of this common core group. A search of protein sequence databases revealed two gene products of DNA sequences from *Caenorhabditis elegans* and from *Saccharomyces cerevisiae* with higher levels of similarity than Sm G protein (see FIGS. 3B and 3C). These two homologs of CaSm gene products also contain Sm motifs and are most similar to CaSm in those regions. These gene products are respectively, deduced from *C. elegans* open reading frame J0714 (PIR S55137) in cosmid F40F8 (GenBank accession number Z69302) and *S. cerevisiae* gene product ORF YJL124c as encoded by the DNA clone with accession number Z49399. The *C. elegans* sequence is 54.4% identical and 72.8% similar over amino acids 3–121, while the *S. cerevisiae* clone is 37.8% identical and 67.7% similar over amino acids 4–130. Both of the Sm motifs are included in these regions. Furthermore, the important amino acids that form the consensus are conserved here as well. Thus, these two proteins which also have a molecular weight similar to CaSm are examples of non-mammalian homologs of CaSm in the respective organisms.

A genetically engineered DNA construct encoding a fusion protein comprising CaSm and a peptide containing the FLAG epitope was transiently transfected in COS-1 cells. The expression of the fusion protein and its intracellular distribution was analyzed by immunofluorescence using antibodies specific for the FLAG epitope (Kodak scientific imaging system). Both cytoplasmic and nuclear staining were observed, although typically not in the same transfected cell. The results suggest that CaSm is an intracellular protein that shuttles between the cytoplasm and the nucleus. Expression experiments performed with a fusion protein comprising CaSm and green fluorescent protein (CaSm-GFP) produced similar results.

7. EXAMPLE

Functional Characterization of the CaSm Gene

This example illustrates the association of CaSm gene expression with the transformed phenotype in pancreatic cancer cells. A soft agar growth assay was used to assess the anchorage independence growth of cancer cells, while the tumorigenicity of cancer cells was tested in mice.

7.1. Materials and Methods

The insert from CaSm was subcloned in the antisense orientation into the eukaryotic expression vector pSGneoSK, which is a modification of pSG5 (Stratagene, La Jolla, Calif.) containing a neomycin/G418-resistance cassette and the multiple cloning site from pBluescript II SK. This construct was used for the transfection of PANC-1 cells. A similar antisense CaSm expression construct was used for transfection of another pancreatic cell line, ASPC-1 cells.

An antisense CaSm expression construct was prepared in *E. coli* using the adenoviral transfer vector, pAdBM5 (Quantum Biotechnologies, Inc., Quebec, Canada), which contains a combination of enhancers and the adenovirus major late promoter, and a cloning site flanked by a recombination sequence. The adenoviral antisense CaSm construct is replication defective except in cells, such as human 293 cells, which complement the deletion in the essential viral E1A and E1B genes. The construct was co-transfected with a portion of the adenovirus 5 genome that has been engineered so that the product of recombination between the two DNA molecules yielded recombinant infectious adenoviruses. These recombinant viruses can be used to infect many different cell lines or tissues of human and non-human origin but they do not replicate after entry into a cell.

7.2. Results

In order to assess whether up-regulation of CaSm in pancreatic cancer cells is related to the transformed state of these cells, we performed an mRNA "knock-down" experiment. An expression construct that constitutively expresses an 0.8 kb antisense RNA of CaSm was stably transfected into PANC-1 cells. After selection in G418 for stable uptake of the construct, individual clones were screened by northern blot hybridization for a decrease in the expression of the endogenous 1.2 kb CaSm mRNA. Since, antisense RNA is expected to interfere primarily with mRNA translation, most of the clones screened did not show any decrease in the level of the endogenous 1.2 kb CaSm mRNA. However, in order to assure that CaSm expression was reduced, clones that showed "knock-down" of the endogenous mRNA were preferentially selected for further study. FIG. 4 shows that several clones were obtained in which the endogenous CaSm mRNA transcript was significantly reduced in the presence of the antisense transcript (0.8 kb).

Four clones, along with the parental cells, were chosen for analysis of anchorage independent growth. A significant decrease in the ability of the antisense transfectants to grow in soft agar was observed (FIG. 5). After three weeks in soft agar, only the parental cell line, PANC-1, retained the ability to produce large colonies in the agar (FIG. 5A). All four antisense transfectants (clones K, L, 1 and 2) failed to produce large colonies, including clone 1, which still expresses some of the endogenous CaSm transcript. Specific quantitation of anchorage independent colony formation for clone K shows that the reduction of large (>280 µm) and medium (140–280 µm) colonies is significantly higher than for small colonies (<140 µm) (FIG. 5B). The reduction of colony formation in soft agar does not appear to be due to growth rate since clone K and the parental cell line PANC-1 have very similar growth rates when grown on plastic.

Similar results were obtained when ASPC-1 cells transfected with an antisense CaSm expression construct were tested in the soft agar assay. The growth of transfectants in soft agar were severely limited in comparison to the parent ASPC-1 cells. The transfected ASPC-1 cells were also tested in vivo to assess their ability to form tumors. Transfected ASPC-1 cells were injected into mice with severe combined immunodeficiency (SCID) which lack cellular and humoral immunity. The results showed that transfected ASPC-1 cells failed to form tumors or formed tumors at a reduced rate in SCID mice when compared to the parent ASPC-1 cells.

Recombinant infectious adenovirus carrying an antisense CaSm expression construct was generated and used to infect naive PANC-1 cells and PANC-1 cells stably transfected with the antisense CaSm construct, as well as naive ASPC-1 cells and ASPC-1 cells stably transfected with the antisense CaSm construct. Both naive PANC-1 and ASPC-1 cells, and transfected PANC-1 and ASPC-1 cells were infected by the recombinant virus, but the infected naive PANC-1 cells and infected naive ASPC-1 cells did not survive in culture. Infected PANC-1 and ASPC-1 cells that have previously been transfected survived and continued to show reduced growth in soft agar.

7.3. Discussion

The results described above show that the CaSm gene is up-regulated in pancreatic cancer tissues and cell lines, and that antisense RNA-induced inhibition of expression of CaSm in pancreatic cancer cell lines dramatically reduces the ability of these cells to form anchorage independent colonies in soft agar. These observations support the idea that CaSm expression in pancreatic epithelia contributes to the transformed state in pancreatic cancer. Since CaSm expression is not induced by serum stimulation in PANC-1 cells or in NIH3T3 cells, and stable transfectants expressing CaSm antisense RNA grow at essentially the same rate as untransfected cells, a direct role in growth regulation seems unlikely.

A large majority of the pancreatic cancer samples examined show elevated expression of CaSm mRNA. However, two of the samples that show upregulation of CaSm compared to matched normal tissue are not neoplastic tissues; rather, they are pancreatitis samples (See FIG. 1). A possible explanation for this observation is that CaSm may also be elevated in pancreatitis, as a predisposing condition to pancreatic cancer (1995, Bansal et al., Gastroent., 109:247–251). Alternatively, the samples tested may contain occult pancreatic cancer. The other possibility is that since high levels of expression of CaSm in activated lymphocytes (see FIG. 2B) has been observed, it could be that the apparent up-regulation detected in pancreatitis is due to the large number of activated lymphocytes that are part of the inflammatory response.

However, preliminary results of experiments with other cell lines, such as prostate cell lines and lung cancer cell lines, suggest that CaSm do play a role in the transformation of these cancer cell lines, thus further supporting the observation in pancreatic cancer.

The feasibility of using gene therapy to treat cancer has also been tested. The strategy is based on delivering antisense CaSm nucleic acid molecules to cancer cells in a patient which causes downregulation of endogenous CaSm gene expression in vivo, and results in tumor regression in the patient. The above described results suggested that an antisense CaSm nucleic acid molecule can be delivered to pancreatic cancer cells by use of an adenovirus-based vector system, and that it could cause a change in the phenotype of the infected cancer cells. Moreover, the result obtained in the SCID mouse model correlates with observations made in the in vitro soft agar growth assay, and indicates that pancreatic cancer cells in which CaSm expression is inhibited by antisense RNA are less tumorigenic in vivo.

8. Deposit of Microorganisms

E. coli strain DH5α, containing a clone of a cDNA encoding CaSm was deposited on Jul. 11, 1997 with the American Type Culture Collection (ATCC), 12301 Parklawn Drive, Rockville, Md. 20852, under the provisions of the Budapest Treaty on the International Recognition of the Deposit of Microorganisms for the Purposes of Patent Procedures, and bears the ATCC accession number 98497.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated nucleic acid molecule comprising the nucleotide sequence of FIG. 6 (SEQ ID NO:7).

\* \* \* \* \*

SEQUENCE LISTING

<160> NUMBER OF SEQ ID NOS: 19

<210> SEQ ID NO 1
<211> LENGTH: 133
<212> TYPE: PRT
<213> ORGANISM: Homo sapiens

<400> SEQUENCE: 1

Met Asn Tyr Met Pro Gly Thr Ala Ser Leu Ile Glu Asp Ile Asp Lys
 1               5                  10                  15

Lys His Leu Val Leu Leu Arg Asp Gly Arg Thr Leu Ile Gly Phe Leu
            20                  25                  30

Arg Ser Ile Asp Gln Phe Ala Asn Leu Val Leu His Gln Thr Val Glu
        35                  40                  45

Arg Ile His Val Gly Lys Lys Tyr Gly Asp Ile Pro Arg Gly Ile Phe
    50                  55                  60

Val Val Arg Gly Glu Asn Val Val Leu Leu Gly Glu Ile Asp Leu Glu
65                  70                  75                  80

Lys Glu Ser Asp Thr Pro Leu Gln Gln Val Ser Ile Glu Glu Ile Leu
                85                  90                  95

Glu Glu Gln Arg Val Glu Gln Gln Thr Lys Leu Glu Ala Glu Lys Leu
            100                 105                 110

Lys Val Gln Ala Leu Lys Asp Arg Gly Leu Ser Ile Pro Arg Ala Asp
        115                 120                 125

Thr Leu Asp Glu Tyr

130

<210> SEQ ID NO 2
<211> LENGTH: 76
<212> TYPE: PRT
<213> ORGANISM: Homo sapiens

<400> SEQUENCE: 2

Met Ser Lys Ala His Pro Pro Glu Leu Lys Lys Phe Met Asp Lys Lys
1               5                   10                  15

Leu Ser Leu Lys Leu Asn Gly Gly Arg His Val Gln Gly Ile Leu Arg
            20                  25                  30

Gly Phe Asp Pro Phe Met Asn Leu Val Ile Asp Glu Cys Val Glu Met
        35                  40                  45

Ala Thr Ser Gly Gln Gln Asn Asn Ile Gly Met Val Val Ile Arg Gly
    50                  55                  60

Asn Ser Ile Ile Met Leu Glu Ala Leu Glu Arg Val
65                  70                  75

<210> SEQ ID NO 3
<211> LENGTH: 119
<212> TYPE: PRT
<213> ORGANISM: Homo sapiens

<400> SEQUENCE: 3

Tyr Met Pro Gly Thr Ala Ser Leu Ile Glu Asp Ile Asp Lys Lys His
1               5                   10                  15

Leu Val Leu Leu Arg Asp Gly Arg Thr Leu Ile Gly Phe Leu Arg Ser
            20                  25                  30

Ile Asp Gln Phe Ala Asn Leu Val Leu His Gln Thr Val Glu Arg Ile
        35                  40                  45

His Val Gly Lys Lys Tyr Gly Asp Ile Pro Arg Gly Ile Phe Val Val
    50                  55                  60

Arg Gly Glu Asn Val Val Leu Leu Gly Glu Ile Asp Leu Glu Lys Glu
65                  70                  75                  80

Ser Asp Thr Pro Leu Gln Gln Val Ser Ile Glu Glu Ile Leu Glu Glu
            85                  90                  95

Gln Arg Val Glu Gln Gln Thr Lys Leu Glu Ala Glu Lys Leu Lys Val
            100                 105                 110

Gln Ala Leu Lys Asp Arg Gly
        115

<210> SEQ ID NO 4
<211> LENGTH: 117
<212> TYPE: PRT
<213> ORGANISM: Caenorhabditis elegans

<400> SEQUENCE: 4

Tyr Leu Pro Gly Ala Ile Ser Leu Phe Glu Gln Leu Asp Lys Lys Leu
1               5                   10                  15

Leu Val Val Leu Arg Asp Gly Arg Lys Leu Ile Gly Phe Leu Arg Ser
            20                  25                  30

Ile Asp Gln Phe Ala Asn Leu Ile Leu Glu Asp Val Val Glu Arg Thr
        35                  40                  45

Phe Val Glu Lys Tyr Phe Cys Glu Thr Gly Gln Gln Gly Phe Met Leu
    50                  55                  60

Ile Arg Gly Glu Asn Val Glu Leu Ala Gly Glu Ile Asp Asp Thr Ile
65                  70                  75                  80

```
Glu Thr Gly Leu Thr Gln Val Ser Pro Glu Glu Phe Arg Arg Leu Glu
                85                  90                  95

Asp Glu Tyr Ile Ala Lys Asn Pro Pro Lys Phe Leu Lys Arg Gln Ala
            100                 105                 110

Glu Lys Thr Glu Glu
        115

<210> SEQ ID NO 5
<211> LENGTH: 127
<212> TYPE: PRT
<213> ORGANISM: Homo sapiens

<400> SEQUENCE: 5

Met Pro Gly Thr Ala Ser Leu Ile Glu Asp Ile Asp Lys Lys His Leu
  1               5                  10                  15

Val Leu Leu Arg Asp Gly Arg Thr Leu Ile Gly Phe Leu Arg Ser Ile
                20                  25                  30

Asp Gln Phe Ala Asn Leu Val Leu His Gln Thr Val Glu Arg Ile His
            35                  40                  45

Val Gly Lys Lys Tyr Gly Asp Ile Pro Arg Gly Ile Phe Val Val Arg
        50                  55                  60

Gly Glu Asn Val Val Leu Leu Gly Glu Ile Asp Leu Glu Lys Glu Ser
 65                  70                  75                  80

Asp Thr Pro Leu Gln Gln Val Ser Ile Glu Glu Ile Leu Glu Glu Gln
                85                  90                  95

Arg Val Glu Gln Gln Thr Lys Leu Glu Ala Glu Lys Leu Lys Val Gln
            100                 105                 110

Ala Leu Lys Asp Arg Gly Leu Ser Ile Pro Arg Ala Asp Thr Leu
        115                 120                 125

<210> SEQ ID NO 6
<211> LENGTH: 133
<212> TYPE: PRT
<213> ORGANISM: Saccharomyces cerevisiae

<400> SEQUENCE: 6

Phe Thr Thr Thr Ala Ala Ile Val Ser Ser Val Asp Arg Lys Ile Phe
  1               5                  10                  15

Val Leu Leu Arg Asp Gly Arg Met Leu Phe Gly Val Leu Arg Thr Phe
                20                  25                  30

Asp Gln Tyr Ala Asn Leu Ile Leu Gln Asp Cys Val Glu Arg Ile Tyr
            35                  40                  45

Phe Ser Glu Glu Asn Lys Tyr Ala Glu Glu Asp Arg Gly Ile Phe Met
        50                  55                  60

Ile Arg Gly Glu Asn Val Val Met Leu Gly Glu Val Asp Ile Asp Lys
 65                  70                  75                  80

Glu Asp Gln Pro Leu Glu Ala Met Glu Arg Ile Pro Phe Lys Glu Ala
                85                  90                  95

Trp Leu Thr Lys Gln Lys Asn Asp Glu Lys Arg Phe Lys Glu Glu Thr
            100                 105                 110

His Lys Gly Lys Lys Met Ala Arg His Gly Ile Val Tyr Asp Phe His
        115                 120                 125

Lys Ser Asp Met Tyr
        130

<210> SEQ ID NO 7
```

-continued

```
<211> LENGTH: 894
<212> TYPE: DNA
<213> ORGANISM: Homo sapiens
<220> FEATURE:
<221> NAME/KEY: CDS
<222> LOCATION: (165)..(563)

<400> SEQUENCE: 7
cttccggcag gccccgccgg cggctgaaag ccggggcaga agtgctggtc tcggtcggga      60
ttccgggctt ggtcccaccg aggcggcgac tgcggtagga gggaactggt tttggacgcg     120
ctggcgtccc gccgctgtgc attgcagcat tatttcagtt caaa atg aac tat atg      176
                                                 Met Asn Tyr Met
                                                  1 cct ggc acc gcc agc ctc atc gag gac att gac aaa aag cac ttg gtt       224
Pro Gly Thr Ala Ser Leu Ile Glu Asp Ile Asp Lys Lys His Leu Val
 5                  10                  15                  20 ctg ctt cga gat gga agg aca ctt ata ggc ttt tta aga agc att gat       272
Leu Leu Arg Asp Gly Arg Thr Leu Ile Gly Phe Leu Arg Ser Ile Asp
             25                  30                  35 caa ttt gca aac tta gtg cta cat cag act gtg gag cgt att cat gtg       320
Gln Phe Ala Asn Leu Val Leu His Gln Thr Val Glu Arg Ile His Val
         40                  45                  50 ggc aaa aaa tac ggt gat att cct cga ggg att ttt gtg gtc agg gga       368
Gly Lys Lys Tyr Gly Asp Ile Pro Arg Gly Ile Phe Val Val Arg Gly
     55                  60                  65 gaa aat gtg gtc cta cta gga gaa ata gac ttg gaa aag gag agt gac       416
Glu Asn Val Val Leu Leu Gly Glu Ile Asp Leu Glu Lys Glu Ser Asp
 70                  75                  80 aca ccc ctc cag caa gta tcc att gaa gaa att cta gaa gaa caa agg       464
Thr Pro Leu Gln Gln Val Ser Ile Glu Glu Ile Leu Glu Glu Gln Arg
 85                  90                  95                 100 gtg gaa cag cag acc aag ctg gaa gca gag aag ttg aaa gtg cag gcc       512
Val Glu Gln Gln Thr Lys Leu Glu Ala Glu Lys Leu Lys Val Gln Ala
                 105                 110                 115 ctg aag gac cga ggt ctt tcc att cct cga gca gat act ctt gat gag       560
Leu Lys Asp Arg Gly Leu Ser Ile Pro Arg Ala Asp Thr Leu Asp Glu
             120                 125                 130 tac taatcttttg cccagaggct gttggctctt gaagagtagg ggctgtcact            613
Tyr gagtgaaagt gacatcctgg ccacctcacg catttgatca cagactgtag agttttgaaa    673
agtcactttt attttaatt attttacata tgcaacatga agaaatcgtg taggtgggtt     733
ttttttttaa ataacaaaat cactgtttaa agaaacagtg gcatagactc cttcacacat    793
cactgtggca ccagcaacta cttctttata ttgttcttca tatcccaaat tagagtttac    853
agggacagtc ttcatttact tgtaaataaa atatgaatct c                        894

<210> SEQ ID NO 8
<211> LENGTH: 133
<212> TYPE: PRT
<213> ORGANISM: Homo sapiens

<400> SEQUENCE: 8

Met Asn Tyr Met Pro Gly Thr Ala Ser Leu Ile Glu Asp Ile Asp Lys
 1               5                  10                  15

Lys His Leu Val Leu Leu Arg Asp Gly Arg Thr Leu Ile Gly Phe Leu
             20                  25                  30

Arg Ser Ile Asp Gln Phe Ala Asn Leu Val Leu His Gln Thr Val Glu
         35                  40                  45
```

```
Arg Ile His Val Gly Lys Lys Tyr Gly Asp Ile Pro Arg Gly Ile Phe
    50                  55                  60

Val Val Arg Gly Glu Asn Val Val Leu Leu Gly Glu Ile Asp Leu Glu
 65                  70                  75                  80

Lys Glu Ser Asp Thr Pro Leu Gln Gln Val Ser Ile Glu Glu Ile Leu
                 85                  90                  95

Glu Glu Gln Arg Val Gln Gln Thr Lys Leu Glu Ala Glu Lys Leu
            100                 105                 110

Lys Val Gln Ala Leu Lys Asp Arg Gly Leu Ser Ile Pro Arg Ala Asp
            115                 120                 125

Thr Leu Asp Glu Tyr
        130

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
cattttgaac tgaaata                                                      17

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
cattttgaac tgaaataatg ctgc                                              24

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
cattttgaac tgaaataatg ctgcaatgca c                                      31

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
cattttgaac tgaaataatg ctgcaatgca cagcggcg                               38

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide
```

<400> SEQUENCE: 13
gttcattttg aactgaaata atgctgcaat gcac        34

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
tttgaactga aataatgctg caatgcacag cggcg        35

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
taatgctgca atgcac        16

<210> SEQ ID NO 16
<211> LENGTH: 33
<212> TYPE: DNA
<213> ORGANISM: Artificial Sequence
<220> FEATURE:
<223> OTHER INFORMATION: Description of Combined DNA/RNA Molecule:
      Ribozyme
<220> FEATURE:
<221> NAME/KEY: modified_base
<222> LOCATION: all "n" positions
<223> OTHER INFORMATION: n=a, c, g, t, or u

<400> SEQUENCE: 16
gttcaaagcn gnnnnnncng agnagucttg aac        33

<210> SEQ ID NO 17
<211> LENGTH: 33
<212> TYPE: DNA
<213> ORGANISM: Artificial Sequence
<220> FEATURE:
<223> OTHER INFORMATION: Description of Combined DNA/RNA Molecule:
      Ribozyme
<220> FEATURE:
<221> NAME/KEY: modified_base
<222> LOCATION: all "n" positions
<223> OTHER INFORMATION: n=a, c, g, t, or u

<400> SEQUENCE: 17
aggcaaagcn gnnnnnncng agnagucata gtt        33

<210> SEQ ID NO 18
<211> LENGTH: 33
<212> TYPE: DNA
<213> ORGANISM: Artificial Sequence
<220> FEATURE:
<223> OTHER INFORMATION: Description of Combined DNA/RNA Molecule:
      Ribozyme
<220> FEATURE:
<221> NAME/KEY: modified_base
<222> LOCATION: all "n" positions
<223> OTHER INFORMATION: n=a, c, g, t, or u

<400> SEQUENCE: 18

```
ctgcaaagcn gnnnnnncng agnaguctgc aca                      33
```

<210> SEQ ID NO 19
<211> LENGTH: 33
<212> TYPE: DNA
<213> ORGANISM: Artificial Sequence
<220> FEATURE:
<223> OTHER INFORMATION: Description of Combined DNA/RNA Molecule:
      Ribozyme
<220> FEATURE:
<221> NAME/KEY: modified_base
<222> LOCATION: all "n" positions
<223> OTHER INFORMATION: n=a, c, g, t, or u

<400> SEQUENCE: 19

```
cgccaaagcn gnnnnnncng agnaguccgc gtc                      33
```